US008318638B2

(12) United States Patent
Yokoyama et al.

(10) Patent No.: US 8,318,638 B2
(45) Date of Patent: Nov. 27, 2012

(54) PLANT ACTIVATOR

(75) Inventors: Mineyuki Yokoyama, Yokohama (JP);
Shoko Yamaguchi, Yokohama (JP);
Toshii Iida, Yokohama (JP); Kiyotaka Kojima, Kakegawa (JP); Koji Kobayashi, Yokohama (JP); Osamu Tanaka, Joyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 12/960,656

(22) Filed: Dec. 6, 2010

(65) Prior Publication Data

US 2011/0152101 A1 Jun. 23, 2011

Related U.S. Application Data

(60) Continuation of application No. 12/011,322, filed on Jan. 25, 2008, now abandoned, which is a continuation of application No. 11/058,368, filed on Feb. 16, 2005, now abandoned, which is a division of application No. 10/069,173, filed as application No. PCT/JP00/05614 on Aug. 22, 2000, now Pat. No. 6,987,130.

(30) Foreign Application Priority Data

Aug. 23, 1999 (JP) .................................... 11-236210

(51) Int. Cl.
*A01N 37/00* (2006.01)
*A61K 31/19* (2006.01)
(52) U.S. Cl. .......................... 504/161; 504/320; 504/560
(58) Field of Classification Search ........................ None
See application file for complete search history.

(56) References Cited

U.S. PATENT DOCUMENTS 6,057,157 A * 5/2000 Yokoyama et al. ........... 435/430

FOREIGN PATENT DOCUMENTS

EP 823 994 * 2/1998

OTHER PUBLICATIONS

European Patent Office, "Communication pursuant to Article 96(2) EPC" issued in European counterpart application, Jan. 23, 2003.
The Patent Office of the People'S Republic of China, "Notification of the First Office Action" issued in Chinese counterpart application, Apr. 23, 2004.
The Patent Office of the People'S Republic of China, "Notification of the Second Office Action" issued in Chinese counterpart application, Apr. 1, 2005.
The Patent Office of the People'S Republic of China, "Notification of the Rejection Decision" issued in Chinese counterpart application, Oct. 14, 2005.
Taiwan Intellectual Property Office, "First Office Action" issued in Taiwanese counterpart application, Sep. 5, 2003.

* cited by examiner

*Primary Examiner* — Alton Pryor

(57) ABSTRACT

An object of the present invention is to determine novel means of activating plants; more particularly, means of controlling plant growth, such as means of promoting growth, means of controlling dormancy, means of imparting tolerance against stress for plants (dryness, high or low temperatures, osmotic pressure, etc.), and means of preventing aging. The present inventors have found that the above object can be achieved by providing plant activators containing, as an active ingredient, $C_4$-$C_{24}$ ketol fatty acids, in particular, 9-hydroxy-10-oxo-12(Z),15(Z)-octadecadienoic acid.

12 Claims, 10 Drawing Sheets

Plant Width of Broad Bean

Plant Height of Eustoma russellianum

Change of Plant Height of Dianthus caryophyllus

Ratio of Dormant Strawberry

Proliferation Effect on Hypha

PLANT ACTIVATOR

CROSS REFERENCE TO A RELATED APPLICATIONS

This is a continuation patent application of application Ser. No. 12/011,322, filed Jan. 25, 2008, now abandoned, which is a continuation patent application of application Ser. No. 11/058,368, filed Feb. 16, 2005, now abandoned, which is a divisional application of application Ser. No. 10/069,173, now patented, which is a national stage application of International Application No. PCT/JP00/05614, filed Aug. 22, 2000.

TECHNICAL FIELD

The present invention relates to a plant activator.

BACKGROUND ART

Development of techniques for activating plants is a very important issue for improving supply efficiency of grain plants and garden plants.

Factors for determining growth rate of plants include temperature, light, and nutrients. Conventionally, in order to promote growth of plants, temperature conditions and sunlight irradiation conditions have been controlled in accordance with characteristics of plants to be grown. Along with techniques utilizing temperature or light, manuring is a typical technique for promoting growth of plants. Manuring has exerted reliable effects.

However, the effect of manuring is limited, and even when the amount of fertilizers employed is increased, the effect of promoting growth of plants to a higher level cannot be expected. Employment of excessive amounts of fertilizers may not only inhibit growth of plants, but also induce contamination of soil.

Particularly, at an early stage of growth of a plant, growth disorder attributed to manuring tends to occur, and therefore manuring is generally not performed at this stage.

An object to be achieved by the present invention is to determine means for activating plants different from conventional activating means; specifically, means for controlling growth of plants, such as means for promoting growth of plants, means for preventing dormancy of plants, means for imparting to plants tolerance against stresses (e.g., dryness, high or low temperatures, and osmotic, pressure), and means for preventing aging of plants, to thereby potentiate plants, with the amounts of fertilizers employed being reduced and contamination of soil being prevented.

DISCLOSURE OF THE INVENTION

In order to achieve the object, the present inventors have performed extensive studies. As a result, the present inventors have found that, surprisingly, a specific ketol fatty acid exerting "the effect of promoting flower bud formation" (see Japanese Patent Application Laid-Open (kokai) No. 11-29410) also exerts "the effect of activating plants," which is, in a sense, contrastive to the effect of promoting flower bud formation. The present invention has been accomplished on the basis of this finding.

Accordingly, the present invention provides a plant activator comprising a $C_4$-$C_{24}$ ketol fatty acid as an active ingredient (hereinafter the activator may be referred to as "the present plant activator").

As used herein, the expression "activation of Plants" refers to controlling plant growth in a certain manner so as to activate or maintain growth of plants, and encompasses actions for controlling plant growth, such as promotion of growth (including increase of size of stems and leaves and promotion of growth of tubers and tuberous roots), control of dormancy, impartment of tolerance against stresses, and prevention of aging. "Activation of plants" is, in a sense, contrastive to "promotion of flower bud formation" described in Japanese Patent Application Laid-Open (kokai) No 11-29410. Formation of flower buds is a phenomenon associated with suppressing life activity of plants. In general, flower buds are formed when growth of plants is inhibited. As is well known in the horticultural field, when blooming of flowers is desired, the following operations—which are considered to arrest growth of plants—are performed: (1) the amount of a nitrogenous fertilizer employed is reduced, (2) the frequency of water sprinkling is reduced, (3) roots are cut, and (4) damage is inflicted to stems. Formation of flowers is a generative phenomenon at a mature stage of plants for transmitting their genes to the next generation, and requires a large amount of energy.

As described above, the aforementioned ketol fatty acid exerting the effect of promoting flower bud formation quite unexpectedly exerts the effect of activating plants.

BEST MODE FOR CARRYING OUT THE INVENTION

Figure 1:
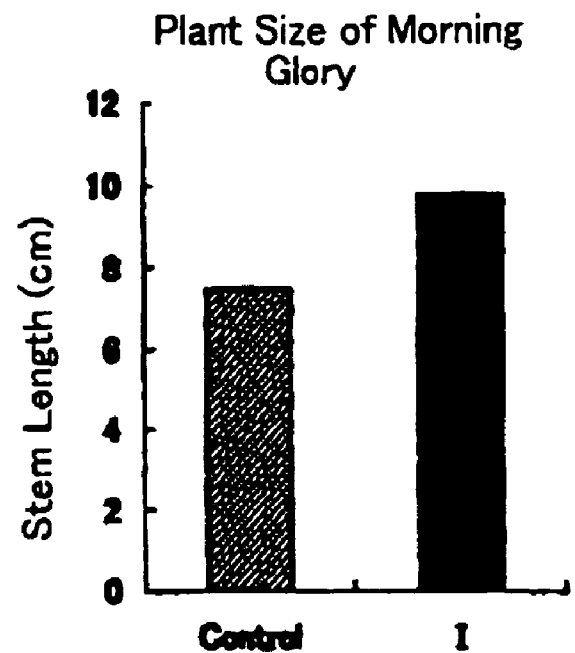
FIG. 1 shows the results of evaluation of growth promotion effect of specific ketol fatty acid (I) on morning glory.

Embodiments of the present invention will next be described.

The present plant activator contains a specific ketol fatty acid as an active ingredient.

As described above, the ketol fatty acid is a $C_4$-$C_{24}$ ketol fatty acid (hereinafter the ketol fatty acid may be referred to as "the specific ketol fatty acid").

Briefly, the specific ketol fatty acid is a $C_4$-$C_{24}$ fatty acid having a hydroxyl group of alcohol and a carbonyl group of ketone in the molecule.

In the present invention, preferably, the specific ketol fatty acid contains the carbon atom constituting the carbonyl group and the carbon atom connected to the hydroxyl group at an α or γ position, in order to exert desired effects of potentiating plants. From this viewpoint, particularly preferably, the carbon atoms are present at an α position.

The specific ketol fatty acid preferably contains one to six carbon-carbon double bonds (note: the number of the double bonds does not exceed the number of carbon-carbon bonds in the ketol fatty acid), in order to exert desired effects of potentiating plants.

Preferably, the specific ketol fatty acid contains 18 carbon atoms, and two carbon-carbon double bonds.

Specific examples of the specific ketol fatty acid include 9-hydroxy-10-oxo-12(Z),15(Z)-octadecadienoic acid [hereinafter may be referred to as "specific ketol fatty acid (I)"], 13-hydroxy-12-oxo-9(Z),15(Z)-octadecadienoic acid [hereinafter may be referred to as "specific ketol fatty acid (II)"], 13-hydroxy-10-oxo-11(E),15(Z)-octadecadienoic acid [hereinafter may be referred to as "specific ketol fatty acid (III)"], and 9-hydroxy-12-oxo-10(E),15(Z)-octadecadienoic acid [hereinafter may be referred to as "specific ketol fatty acid (IV)"].

The chemical formulas of specific ketol fatty acids (I) and (IV) are as follows.

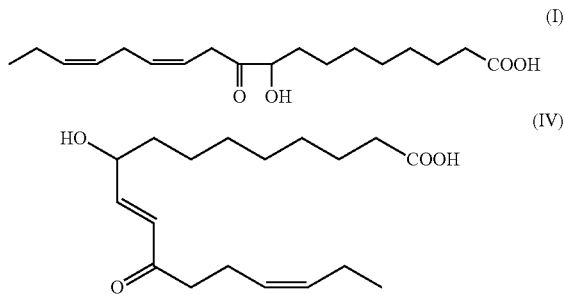

The chemical formulas of specific ketol fatty acids (II) and (III) are described below in connection with the chemical synthesis method of these fatty acids.

Among specific ketol fatty acids, at least same ketol fatty acids are known as metabolic intermediates of fatty acids in animals and plants, but the role that the ketol fatty acids play directly in plants is not known.

For example, specific ketol fatty acid (I) is known as an intermediate in a fatty acid metabolic pathway in which α-linolenic acid, which is abundantly present in living organisms, serves as a starting material. However, the specific role that ketol fatty acid (I) plays directly in plants has remained unknown.

The present inventors have found that the aforementioned ketol unsaturated fatty acids related to the present invention exert the effect of activating plants.

A. Production Method of Specific Ketol Fatty Acid

A desired specific ketol fatty acid can be produced by means of a method in accordance with the specific structure of the fatty acid.

Specifically, (1) a specific ketol fatty acid which is known to be present in a naturally occurring product can be prepared from the product by means of a method in which the naturally occurring product is subjected to extraction and purification (hereinafter the method will be referred to as an "extraction method"); (2) a specific ketol fatty acid can be produced by means of a method in which an unsaturated fatty acid is reacted with an enzyme such as lipoxygenase in a manner similar to that of a fatty acid metabolic pathway in plants (hereinafter the method will be referred to as an "enzyme method"); and (3) a desired specific ketol fatty acid can be produced by means of a known chemical synthesis method in accordance with the specific structure of the fatty acid (hereinafter the method will be referred to as a "chemical synthesis method").

(1) Extraction Method

Specific ketol fatty acid (I) can be obtained from *Lemna paucicostata*, which belongs to Lemnaceae, through extraction and purification.

*Lemna paucicostata* used as a source material in this extraction method is a small water plant floating on the surface of a pond or a paddy field, and each thallus floating on the water forms one root in the water. *Lemna paucicostata* is known to have a relatively fast growth rate. The flower thereof is formed on the side of the thallus in which two male flowers containing only one stamen and a female flower containing one pistil are enveloped in a small common bract.

The homogenate of *Lemna paucicostata* is subjected to centrifugation (8,000×g, about 10 minutes), and the fraction obtained by removing the supernatant from the resultant supernatant and precipitate can be used as a fraction containing specific ketol fatty acid (I).

As described above, specific ketol fatty acid (I) can be isolated and purified from the aforementioned homogenate serving as a starting material.

An aqueous solution obtained by floating or immersing *Lemna paucicostata* in water may be used as a preferred starting material in terms of preparation efficiency. No particular limitation is imposed on the aqueous solution, so long as *Lemna paucicostata* is viable in the solution.

Specific methods for preparing the aqueous solution are described below in Examples.

The immersing time is not particularly limited, and may be about two to three hours at room temperature.

When the starting material of specific ketol fatty acid (I) is prepared by means of the aforementioned method, in consideration of production efficiency of specific ketol fatty acid (I), *Lemna paucicostata* is preferably subjected, in advance, to specific stress which enables induction of specific ketol fatty acid (I).

Specific examples of the aforementioned stress include dry stress, heat stress, and osmotic pressure stress.

The dry stress may be imposed on *Lemna paucicostata*, for example, by allowing *Lemna paucicostata* to spread on a dry paper filter at low humidity (preferably at a relative humidity of 50% or less) and at room temperature, preferably at 24-25° C. In this case, the drying time, which varies with the spreading density of *Lemna paucicostata* to be dried, is about 20 seconds or more, preferably five minutes to five hours.

The heat stress may be imposed on *Lemna paucicostata*, for example, by immersing *Lemna paucicostata* in hot water. In this case, the temperature of hot water is determined in accordance with the immersing time. For example, when the immersing time is about five minutes, the temperature of hot water is 40-65° C., preferably 45-60° C., more preferably 50-55° C. Preferably, immediately after the aforementioned heat stress treatment, *Lemna paucicostata* is returned to water of ambient temperature.

The osmotic pressure stress may be imposed on *Lemna paucicostata*, for example, by bringing *Lemna paucicostata* into contact with a solution of high osmotic pressure, such as a sugar solution of high concentration. In the case, when a mannitol solution is used, the sugar concentration is 0.3 M or more, preferably 0.5-0.7 M. When a 0.5 M mannitol solution is used, the treatment time is one minute or more, preferably two to five minutes.

Thus, a desired starting material containing specific ketol fatty acid (I) can be prepared.

No particular limitation is imposed on the strain of *Lemna paucicostata* serving as a source material of the aforementioned various starting materials, but a strain P441 is particularly preferred when specific ketol fatty acid (I) is to be produced.

A starting material prepared as described above may be subjected to the below-described separation and purification, to thereby produce desired specific ketol fatty acid (I).

The separation method employed for producing specific ketol fatty acid (I) from the aforementioned starting material is not limited to the below-described example separation methods.

Firstly, the aforementioned starting material is preferably subjected to extraction by use of a solvent, to thereby obtain an extract containing specific ketol fatty acid (I). Examples of the solvent include, but are not limited to, chloroform, ethyl acetate, and ethers. Of these solvents, chloroform is preferred, since it enables removal of impurities in a relatively easy manner.

The oil layer fractions obtained through the solvent extraction are washed and concentrated by means of a conventionally known method, and then subjected to high performance liquid chromatography (HPLC) by use of a reversed-phase partition chromatography column such as an ODS (octadecylsilane) column, to thereby identify and isolate a fraction having ability to induce flower bud formation, thereby potentially isolating specific ketol fatty acid (I) [note: the specific ketol fatty acid is known to have ability to induce flower bud formation (see Japanese Patent Application Laid-Open (kokai) No. 10-324602)].

In accordance with properties of the starting material, other conventionally known separation methods, such as ultrafiltration and gel filtration chromatography, may be employed in combination.

The production process of specific ketol fatty acid (1) by means of the extraction method has been described above. When a desired specific ketol fatty acid is present in a plant other than *Lemna paucicostata*, the fatty acid can be produced by means of a method similar to that described above or a modification of the aforementioned method.

(2) Enzyme Method

Typical examples of the starting material employed in the extraction method include $C_4$-$C_{24}$ unsaturated fatty acids having carbon-carbon double bonds at positions corresponding to those of carbon-carbon double bonds contained in a desired specific ketol fatty acid.

Examples of the unsaturated fatty acids include, but are not limited to, oleic acid, vaccenic acid, linoleic acid, α-linolenic acid, γ-linolenic acid, arachidonic acid, 9,11-octadecadienoic acid, 10,12-octadecadienoic acid, 9,12,15-octadecatrienoic acid, 6,9,12,15-octadecatetraenoic acid, 11,14-eicosadienoic acid, 5,8,11-eicosatrienoic acid, 11,14,17-eicosatrienoic acid, 5,8,11,14,17-eicosapentaenoic acid, 13,16-docosadienoic acid, 13,16,19-docosatrienoic acid, 7,10,13,16-docosatetraenoic acid, 7,10,13,16,19-docosapentaenoic acid, and 4,7,10,13,16,19-docosahexaenoic acid.

These unsaturated fatty acids are generally present in animals and plants. The fatty acids may be obtained from animals and plants through extraction and purification by means of conventionally known methods, or may be obtained through chemical synthesis by means of conventionally known methods. Alternatively, the fatty acids may be commercially available products.

In the enzyme method, the aforementioned unsaturated fatty acid serving as a substrate is reacted with lipoxygenase (LOX), to thereby introduce a hydroperoxy group (—OOH) into the carbon chain of the unsaturated fatty acid.

Lipoxygenase is an oxidoreductase which introduces molecular oxygen, as a hydroperoxy group, into the carbon chain of an unsaturated fatty acid. As has been confirmed, lipoxygenase is present in animals and plants, as well as in yeast such as *saccharomyces*.

For example, the presence of lipoxygenase is recognized in plants such as angiosperms [specifically, the below-described dicotyledons and monocotyledons to which the present plant activator can be applied].

Among the aforementioned plants, examples of the particularly preferred origin of lipoxygenase include soybean, flax, alfalfa, barley, broad bean, lupine, lentil, field pea, potato, wheat, apple, bread yeast, cotton, cucumber, gooseberry, grape, pear, kidney bean, rice, strawberry, sunflower, and tea. Since chlorophyll tends to inhibit the aforementioned activity of lipoxygenase, if possible, lipoxygenase is preferably obtained from seeds, roots, fruits, etc. of the plants in which chlorophyll is not present.

In the present invention, lipoxygenase of any origin may be used, so long as it can introduce a hydroperoxy group into a desired position of the carbon chain of an unsaturated fatty acid. However, when specific ketol fatty acid (I) is produced, if possible, lipoxygenase which enables selective oxidation of the carbon-carbon double bond at position 9 of linoleic acid or linolenic acid is preferably used.

Typical examples of the selective lipoxygenase include lipoxygenase derived from rice germ [e.g., Yamamoto, A., Fuji, Y., Yasumoto, K., Mitsuda, H., Agric. Biol. Chem., 44, 443 (1980)].

Preferred examples of the unsaturated fatty acid serving as a substrate with respect to the selective lipoxygenase include linoleic acid and α-linolenic acid.

When an unsaturated fatty acid serving as a substrate is treated with lipoxygenase, enzymatic reaction is preferably allowed to proceed at an optimum temperature and an optimum pH of the lipoxygenase to be employed.

Unwanted impurities generated through the aforementioned lipoxygenase reaction process may be easily separated by means of conventionally known methods, such as HPLC described above in (1).

Lipoxygenase used herein may be obtained from, for example, the aforementioned plants through extraction and purification by means of conventionally known methods, or may be a commercially available product.

Thus, a hydroperoxy unsaturated fatty acid can be produced from the aforementioned unsaturated fatty acid.

The hydroperoxy unsaturated fatty acid may be considered an intermediate in the production process of a specific ketol fatty acid by means of the enzyme method.

Examples of the hydroperoxy unsaturated fatty acid include 9-hydroperoxy-10(E),12(Z),15(Z)-octadecatrienoic acid, which serves as an intermediate of the aforementioned specific ketol fatty acid (I) and can be obtained by reacting α-linolenic acid with lipoxygenase.

Of these hydroperoxy fatty acids, the former 9-hydroperoxy-10(E),12(Z),15(Z)-octadecatrienoic acid will be called "hydroperoxy fatty acid (a)" in relation to the present invention, and the latter 13-hydroperoxy-9(Z),11(E),15(Z)-octadecatrienoic acid will be called "hydroperoxy fatty acid (b)" in relation to the present invention. The chemical formulas of these hydroperoxy fatty acids are described below.

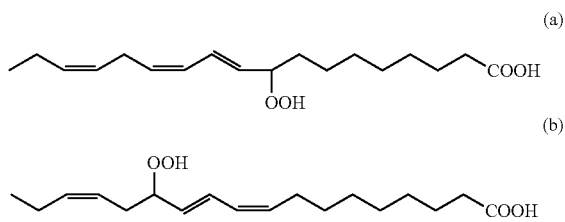

Subsequently, the hydroperoxy unsaturated fatty acid serving as a substrate is reacted with allene oxide synthase, to thereby produce a desired specific ketol fatty acid.

Allene oxide synthase is an enzyme having the activity of converting a hydroperoxy group, via epoxidation, into a ketol structure. Similar to the aforementioned lipoxygenase, allene oxide synthase is present in plants, animals, and yeast. For example, allene oxide synthase is present in plants such as angiosperms (specifically, the below-described dicotyledons and monocotyledons to which the present plant activator can be applied).

The presence of allene oxide synthase is recognized in plants such as barley, wheat, corn, cotton, eggplant, flax (e.g., flax seed), lettuce, oat, spinach, and sunflower.

In the present invention, no particular limitation is imposed on the allene oxide synthase employed, so long as it enables formation of an epoxy group through dehydration of the hydroperoxy group at position 9 of, for example, the aforementioned 9-hydroperoxy-10(E),12(Z), 15(Z)-octadecatrienoic acid, to thereby produce a desired specific ketol fatty acid through nucleophilic reaction of OH⁻.

When the aforementioned allene oxide synthase treatment is performed, enzymatic reaction is preferably allowed to proceed at an optimum temperature and an optimum pH of the allene oxide synthase to be employed.

Allene oxide synthase used herein may be obtained from, for example, the aforementioned plants through extraction and purification by means of conventionally known methods, or may be a commercially available product.

The aforementioned two enzymatic reaction processes may be performed separately or successively. The aforementioned enzymatic reaction may be allowed to proceed by use of the crude or purified product of the aforementioned enzyme, to thereby produce a desired specific ketol fatty acid. Also, the aforementioned enzyme may be immobilized on a carrier, after which the enzyme substrate may be subjected to column treatment or batch treatment by use of the thus-immobilized enzyme, to thereby produce a desired specific ketol fatty acid.

The enzymes employed in the aforementioned two processes may be prepared by means of a genetic engineering technique. Specifically, the enzymes can be produced as follows: genes encoding the enzymes are obtained from, for example, plants through extraction by means of a customary method, or the genes are obtained through chemical synthesis on the basis of the genetic sequence of the enzymes; microorganisms such as *Escherichia coli* and yeast, animal cultured cells, or plant cultured cells are transformed by use of the above-obtained genes; and the recombinant enzyme protein is expressed in the resultant transformed cells.

When a specific ketol fatty acid is produced through nucleophilic reaction of OH⁻ (described above) after formation of an epoxy group, depending on the reaction of the nucleophile in the vicinity of the epoxy group, a γ-ketol compound is formed in addition to an α-ketol unsaturated fatty acid.

The thus-formed γ-ketol compound can be easily separated from the α-ketol compound by means of a conventionally known separation method, such as HPLC described above in (1).

(3) Chemical Synthesis Method

A specific ketol fatty acid may be produced by means of conventionally known chemical synthesis methods.

For example, a saturated carbon chain having, at its one end, a reactive group such as an aldehyde group and having, at the other end, a carboxyl end group connected to a protective group is synthesized by means of a conventionally known method, and separately, an unsaturated carbon chain having, at a desired position, an unsaturated group and having a reactive end group is synthesized from a starting material such as an unsaturated alcohol (e.g., cis-3-hexen-1-ol). Subsequently, the resultant saturated hydrocarbon chain and unsaturated carbon chain are reacted with each other, to thereby produce a specific ketol fatty acid. In the aforementioned reactions, the protective group connected to any end group which does not participate in reaction, and the catalyst for promoting reaction may be appropriately chosen in accordance with the specific reaction mode.

More specifically, specific ketol fatty acids may be synthesized through, for example, the below-described processes.

i) Synthesis of Specific Ketol Fatty Acid (I)

Nonanedioic acid monoethyl ester serving as a starting material is reacted with N,N'-carbonyldiimidazole, to thereby yield an acid imidazolide, and subsequently, the acid imidazolide is reduced by use of LiAlH₄ at low temperature, to thereby synthesize the corresponding aldehyde. The aforementioned starting material may be changed to, for example, a diol such as 1,9-nonanediol, to thereby synthesize a similar aldehyde.

Separately, cis-3-hexen-1-ol is reacted with triphenylphosphine and carbon tetrabromide. The resultant bromide is reacted with triphenylphosphine, and further reacted with chloroacetaldehyde in the presence of n-BuLi, to thereby form a cis olefin. The cis olefin is reacted with methylthiomethyl p-tolyl sulfone, and then reacted with the above-synthesized aldehyde in the presence of n-BuLi, to thereby yield a secondary alcohol. The resultant secondary alcohol is protected by tert-butyldiphenylsilyl chloride (TBDPSCl), and subjected to hydrolysis by use of an acid, and then to deprotection, to thereby synthesize desired specific ketol fatty acid (I).

A brief scheme of an embodiment of the synthesis process of specific ketol fatty acid (I) is described below.

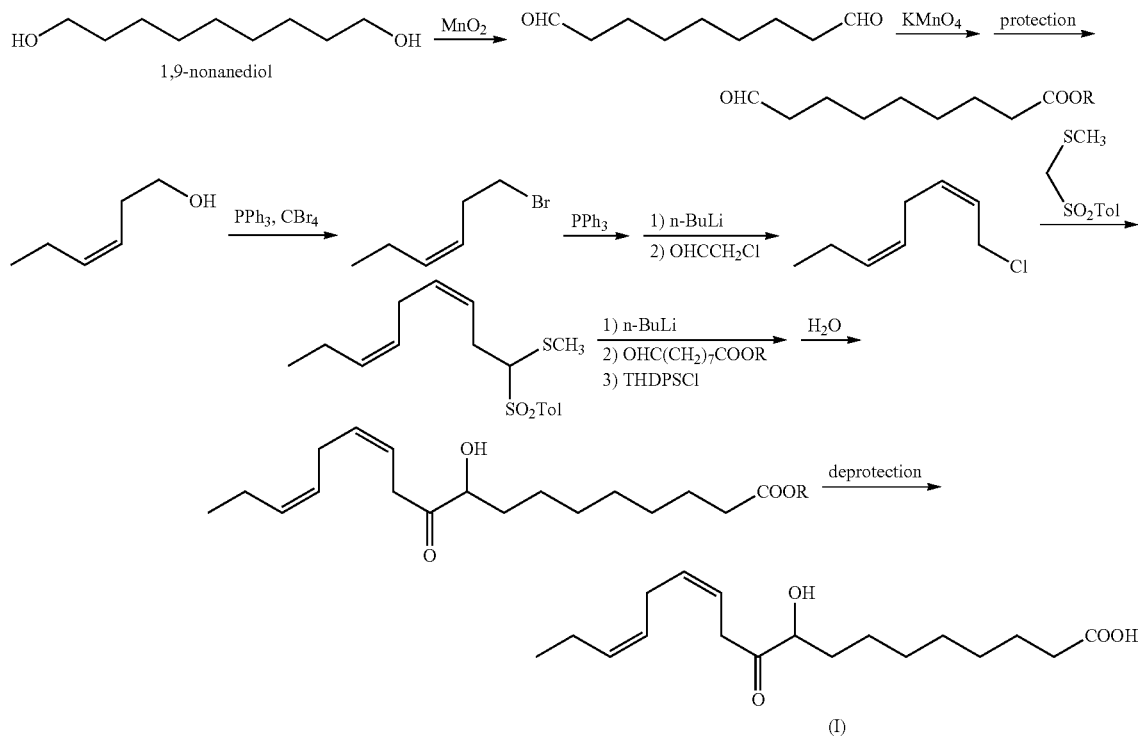

ii) Synthesis of Specific Ketol Fatty Acid (II)

Nonanedioic acid monoethyl ester serving as a starting material is reacted with thionyl chloride, and the resultant acid chloride is reduced by use of NaBH$_4$, to thereby yield an acid alcohol. Subsequently, the free carboxyl group of the resultant acid alcohol is protected, and the resultant product is reacted with triphenylphosphine and carbon tetrabromide. The resultant bromide is reacted with triphenylphosphine, and further reacted with chloroacetaldehyde in the presence of n-BuLi, to thereby form a cis olefin. The cis olefin is reacted with methylthiomethyl p-tolyl sulfone, and then reacted with, in the presence of n-BuLi, an aldehyde which has been obtained through PCC oxidation of cis-3-hexen-1-ol. The resultant product is subjected to deprotection, to thereby accomplish synthesis of desired specific ketol fatty acid (II).

A brief scheme of an embodiment of the synthesis process of specific ketol fatty acid (II) is described below.

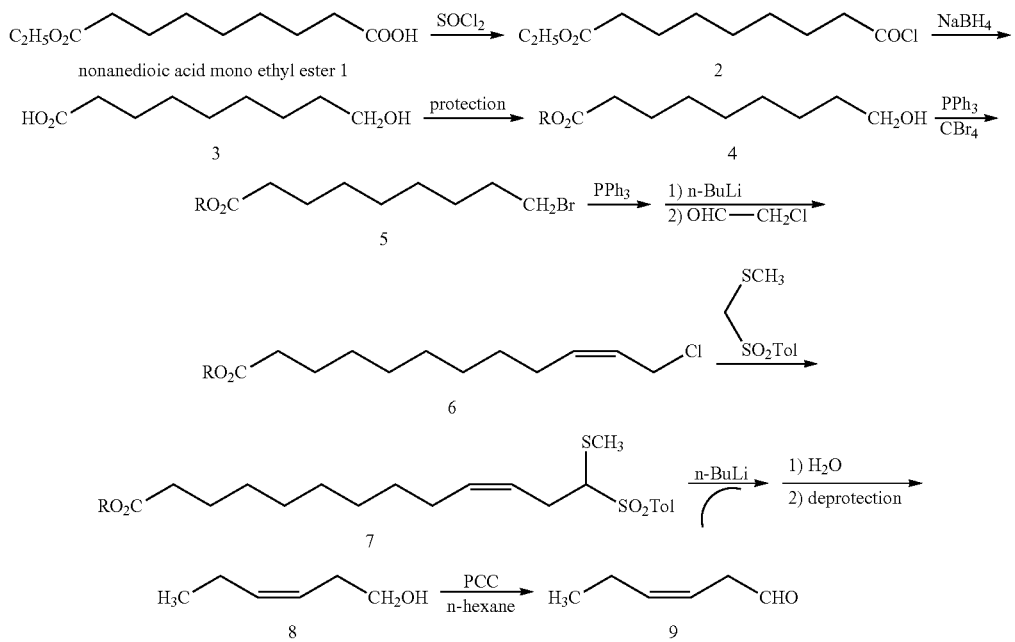

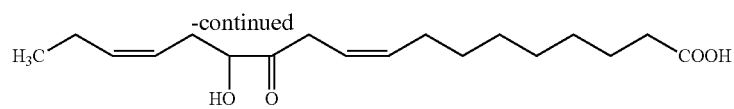

13-hydroxy-12-oxo-9(Z),15(Z)-octadecadienoic acid 10

(II)

iii) Synthesis of Specific Ketol Fatty Acid (III)

Methyl vinyl ketone serving as a starting material is reacted with trimethylsilyl chloride in the presence of LDA and DME. MCPBA and trimethylaminehydrofluoric acid are added to the resultant silyl ether at a low temperature (−70° C.), to thereby prepare a keto-alcohol. Subsequently, the carbonyl group of the keto-alcohol is protected, and then, in the presence of triphenylphosphine and trichloroacetone serving as reaction reagents, reaction is allowed to proceed so as to prevent addition of chlorine to the carbon-carbon double bond. The reaction product is reacted with formic acid in the presence of tributylarsine and $K_2CO_3$, to thereby form a trans olefin and then form a chloride. Subsequently, the resultant chloride is reacted with an aldehyde which has been obtained through PCC oxidation of cis-3-hexen-1-ol. The resultant reaction product is bonded to 6-heptenoic acid, and then subjected to deprotection, to thereby synthesize desired specific ketol fatty acid (III).

A brief scheme of an embodiment of the synthesis process of specific ketol fatty acid (III) is described below.

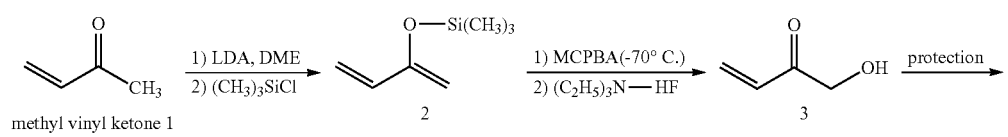

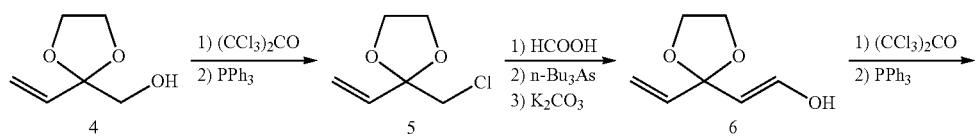

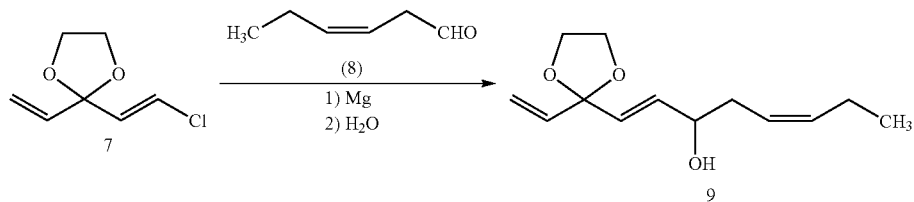

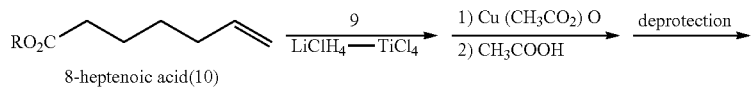

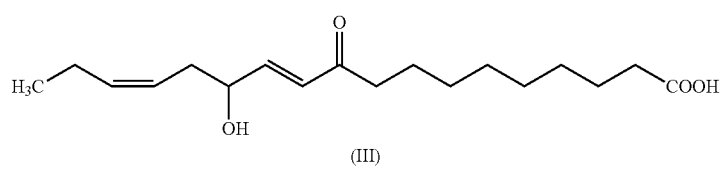

13-hydroxy-10-oxo-11(E),15(Z)-octadecadienoic acid 11

B. The Present Plant Activator

When the present plant activator is applied to a plant, the plant can be activated. Particularly, the present plant activator exerts plant growth controlling effect in various manners so as to activate growth of plants.

"Plant activation effect" and "plant growth controlling effect" will next be described in detail.

(1) Growth Promoting Effect

Application of the present plant activator to a plant can increase the growth rate of the plant and improve harvest efficiency of the plant (as described above, increase of size of stems and leaves and promotion of growth of tubers and tuberous roots can be expected). Accordingly, the present invention also provides a plant growth promoting agent which exerts more specific effect; i.e., effect of promoting growth of plants.

When the present plant activator is used for promoting growth of plants; particularly, promotion of growth of plants at an early stage after germination—which has been difficult to attain by use of a fertilizer—can be attained.

Therefore, when the present plant activator is used as a plant growth promoting agent, application of the activator is preferably carried out during seeding or at an early growth stage after germination.

When the present plant activator is merely applied, for example, through spraying, at an early growth stage after germination, growth of plants is promoted, and the effect of promoting plant growth is maintained. As described above, even when the present plant activator is used in excessive amounts, growth disorder of plants, which occurs when a fertilizer is used in excessive amount, is not observed. Therefore, careful consideration of the amount of the activator to be employed is not necessary.

In the horticultural or agricultural field, instead of distribution of seeds, which require troublesome handling after delivery, distribution of seedlings is becoming the mainstream. Particularly, in the flower business, in most cases, gardening amateurs purchase seedlings. When the present plant activator is employed before distribution of seedlings, the grown seedlings can be sold.

In the case of rice plants, in general, after seedlings are grown in a seedbed at an early stage, the grown seedlings are planted in a paddy field. When the present plant activator is applied to seedlings in a seedbed, the growth of the seedlings is promoted, and the number of stems per strain after planting is increased. In the case of rice plants, the number of spikes per strain can be increased, to thereby enhance harvest efficiency. Similarly, when the present plant activator is employed, the harvest efficiency of other cereal plants such as barley and corn or fabaceous plants such as soybean can be enhanced.

The aforementioned properties of the present plant activator are suitable for increasing the harvest of spinach, lettuce, cabbage, broccoli, or cauliflower.

When the present plant activator is applied to ascomycete or basidiomycete, the growth of hyphae thereof can be promoted, to thereby increase the harvest yield of carpophores (mushrooms: for example, *Lentinus edodes*, oyster mushroom, *Lyophyllum decastes*, mushroom, *Pholiota nameko*, *Grifola frondosa*, and *Celtis sinensis*). Furthermore, the present plant activator may contribute to establishment of an artificial culture method of mushrooms which at present are difficult to culture artificially (e.g., *Tricholoma matsutake*).

(2) Dormancy Preventive Effect

When the present plant activator is applied to a plant, the dormancy of the plant can be prevented. Specifically, when the present plant activator is applied to a plant, the "dormancy period" of the plant during which the growth of the plant is stopped can be reduced or terminated.

Accordingly, the present invention also provides a plant dormancy preventive agent which exerts more specific effect; i.e., effect of preventing dormancy of plants.

In the case in which the present plant activator is used as a plant dormancy preventive agent, when the activator is applied to a plant immediately after germination, the dormancy of the plant can be prevented. Alternatively, the activator may be applied to a dormant plant, to thereby terminate the dormancy of the plant.

(3) Anti-Stress Effect

When the present plant activator is applied to a plant, the plant can be endowed with tolerance against various stresses, such as dry stress, high-temperature stress, low-temperature stress, and osmotic-pressure stress. Briefly, when the present plant activator is employed, there can be reduced the effect of stresses—which are attributed to climate variation, induction of germination of seeds, etc.—on cultivated plants, the stresses potentially causing reduction in yield of the plants.

In this sense, the present invention also provides a plant stress suppressive agent which exerts more specific effect; i.e., effect of suppressing stresses imposed on plants.

In the case in which the present plant activator is used as a plant stress suppressor, when the activator is applied to a plant during germination of its seed or after germination, the plant can be endowed with tolerance against stresses.

Application of the present plant activator to a plant may prevent aging of the plant. For example, if the present plant activator is applied to a therophyte plant which is in the period in which the plant' becomes weak and is dying, weakening (aging) of the therophyte can be retarded.

No particular limitation is imposed on the upper limit of the amount of a specific ketol fatty acid—which is an active ingredient of the present plant activator—applied to plants. Even when a specific ketol fatty acid is applied to plants in a large amount through use of the present plant activator, negative effects on plants, such as growth inhibition, are barely observed. In contrast, when a conventionally used plant hormone agent is excessively applied to plants, considerable negative effects on plants are observed. Therefore, the plant hormone agent must be used carefully so as not to be excessively applied to plants. From this viewpoint, the present plant activator is more advantageous as compared with the conventional plant hormone agent.

The lower limit of the amount of the aforementioned specific ketol fatty acid applied to a single plant, which varies with the type and size of the plant, is about 1 μm per application.

The amount of a specific ketol fatty acid incorporated into the present plant activator may be determined in accordance with use of the activator, the type of a plant to which the activator is to be applied, and the specific product form of the activator. A specific ketol fatty acid may be used as the present plant activator. However, in consideration of the aforementioned lower limit of the application amount of a specific ketol fatty acid, etc., the specific ketol fatty acid is preferably incorporated in an amount of about 0.1-100 ppm, more preferably about 1-50 ppm, on the basis of the entirety of the plant activator.

Examples of the product form of the present plant activator include solutions, solid agents, powders, and emulsions. In accordance with the product form, the present plant activator may appropriately contain known pharmaceutically acceptable carrier components and auxiliary agents for drug production, so long as they do not impede the intended effect of the present invention; i.e., plant growth promoting effect.

When the present plant activator assumes the form of powders or solid agents, for example, the following carrier components may be incorporated: inorganic substances such as talc, clay, vermiculite, diatomaceous earth, kaolin, calcium carbonate, calcium hydroxide, terra alba, and silica gel; and solid carriers such as flour and starch. When the present plant activator assumes the form of solutions, for example, the following carrier components may be incorporated: liquid carriers including water; aromatic hydrocarbons such as xylene; alcohols such as ethanol and ethylene glycols; ketones such as acetone; ethers such as dioxane and tetrahydrofuran; dimethylformamide; dimethyl sulfoxide; and acetonitrile. Examples of the auxiliary agents for drug production which may be incorporated include anionic surfactants such as alkyl sulfates, alkyl sulfonates, alkyl aryl sulfonates, dialkyl sulfosuccinates; cationic surfactants such as salts of higher aliphatic amines; nonionic surfactants such as polyoxyethylene glycol alkyl ethers, polyoxyethylene glycol acyl esters, polyoxyethylene polyalcohol acyl esters, and cellulose derivatives; thickeners such as gelatin, casein, gum arabi; extenders; and binders.

If desired, the present plant activator may further contain typical plant growth controlling agents, benzoic acid, nicotinic acid, nicotinamide, and pipecolic acid, so long as they do not impede the intended effects of the present invention.

The present plant activator may be applied to various plants in a manner in accordance with the product form of the activator. For example, the present plant activator may be sprayed, dropped, or applied, in the form of solution or emulsion, to the point of growth of a plant, to a portion of the plant, such as stem or leaf, or to the entirety of the plant; or may be absorbed, in the form of solid agent or powder, in the root of the plant via earth. Alternatively, when the present plant activator is used for promoting growth of a water plant such as duckweed, the activator may be absorbed in the root of the water plant, or the activator in the form of solid agent may be gradually dissolve in the water.

The frequency of application of the present plant activator to a plant varies with the type of the plant or the purpose of application. Basically, desired effects can be obtained through merely a single application. When the activator is applied several times, application is preferably performed at an interval of one week or more.

No particular limitation is imposed on the type of plants to which the present plant activator can be applied, and the activator is effective for angiosperms (dicotyledons and monocotyledons), fungi, lichens, bryophytes, ferns, and gymnosperms.

Examples of dicotylendos of angiosperms include Convolvulaceae such as *Convolvulus* (*C. nil*), Calystegia (*C. japonica, C. hederacea*, and *C. soldanella*), *Ipomoea* (*I. pescaprae*, and *I. batatas*), and *Cuscuta* (*C. japonica*, and *C. australis*), Caryophyllaceae such as *Dianthus, Stellaria, Minuartia, Cerastium, Sagina, Arenaria, Moehringia, Pseudostellaria, Honkenya, Spergula, Spergularia, Silene, Lychnis, Melandryum*, and *Cucubalus*, and furthermore, Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Mitrastemonaceae, Balanophoraceae, Polygonaceae, Chenopodiaceae, Amaranthaceae, Nyctaginaceae, Theligonaceae, Phytolaccaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Lauraceae, Papaveraceae, Capparaceae, Brassicaceae (Crusiferae), Droseraceae, Nepenthaceae, Crassulaceae, Saxifragaceae, Pittosporaceae, Hamamelidaceae, Platanaceae, Rosaceae, Fabaceae (Leguminosae), Oxalidaceae, Geraniaceae, Linaceae, Zygophyllaceae, Rutaceae, Simaroubaceae, Meliaceae, Polygolaceae, Euphorbiaceae, Callitrichaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, Balsaminaceae, Rhamnaceae, Vitaceae, Elaeocarpaceae, Tiliaceae, Malvales, Sterculiaceae, Actinidiaceae, Theaceae, Clusiaceae (Guttiferae), Elatinaceae, Tamaricaceae, Violaceae, Flacourtiaceae, Stachyuraceae, Possifloraceae, Begoniaceae, Cactaceae, Thymelaeaceae, Elaeagnaceae, Lythraceae, Punicaceae, Rhizophoraceae, Alangiaceae, Melastomataceae, Trapaceae, Onagraceae, Haloragaceae, Hippuridaceae, Araliaceae, Apiaceae (Umbelliferae), Cornaceae, Diapensiaceae, Clethraceae, Pyrolaceae, Ericaceae, Myrsinaceae, Primulaceae, Plumbaginaceae, Ebenaceae, Symplocaceae, Styracaceae, Oleaceae, Buddlejaceae, Gentianaceae, Apocynaceae, Asclepiadaceae, Polemoniaceae, Boraginaceae, Verbenaceae, Lamiaceae (Labiatae), Solanaceae (Solanum, Lycoperisicon, etc.), Scrophulariaceae, Bignoniaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae, and Asteraceae (Compositae).

Examples of monocotyledons include Lemnaceae such as *Spirodela* (*S. polyrhiza*), and *Lemna* (*L. paucicostata*, and *L. trisulcata*), Orchidaceae such as *Cattleya, Cymbidium, Dendrobium, Phalaenopsis, Vanda, Paphiopedilum*, and *Oncidium*, Typhaceae, Sparganiaceae, Potamogetonaceae, Najadaceae, Scheuchzeriaceae, Alismataceae, Hydrocharitaceae, Triuridaceae, Poaceae (Gramineae) (*Oryza, Hordeum, Triticum, Secale, Zea*, etc.), Cyperaceae, Arecaceae (Palmae), Araceae, Eriocaulaceae, Commelinaceae, Pontederiaceae, Juncaceae, Stemonaceae, Liliaceae (Asparagus, etc.), Amaryllidaceae, Dioscoreaceae, Iridaceae, Musaceae, Zingiberaceae, Cannaceae, and Burmanniaceae.

EXAMPLES

The present invention will next be described in detail by way of Examples, which should not be construed as limiting the invention thereto.

Production Example

Production of Specific Ketol Fatty Acid (I)

Specific ketol fatty acid (I) [9-hydroxy-10-oxo-12(Z),15 (Z)-octadecadienoic acid] was produced by means of an enzyme method as follows.

1. Preparation of Rice-Germ-Derived Lipoxygenase

Rice germ (350 g) was washed with petroleum ether, defatted, and then dried. The resultant rice germ (250 g) was suspended in a 0.1 M acetate buffer solution (pH 4.5) (1.25 L), and the resultant suspension was homogenized.

Subsequently, the resultant homogenized extract was subjected to centrifugation at 16,000 rpm for 15 minutes, to thereby yield a supernatant (0.8 L). Ammonium sulfate (140.8 g) (30% saturation) was added to the supernatant, and the resultant mixture was allowed to stand at 4° C. overnight. Thereafter, the mixture was subjected to centrifugation at 9,500 rpm for 30 minutes, to thereby yield a supernatant (0.85 L). Ammonium sulfate (232 g) (70% saturation) was added to the supernatant, after which the resultant mixture was allowed to stand at 4° C. for five hours.

Subsequently, the mixture was subjected to centrifugation at 9,500 rpm for 30 minutes, to thereby yield a precipitate. The above-yielded precipitates (fractions obtained from the rice germ extract through addition of ammonium sulfate (30-70% saturation) were dissolved in an acetate buffer solution (pH 4.5) (300 mL), and then heated at 63° C. for five minutes. Thereafter, the precipitate was removed, and the supernatant was subjected to desalting through dialysis (3 L×3) by use of an RC dialysis tube (Pore 4, product of Spectrum: MWCO 12,000-14,000), to thereby yield a crude solution containing desired rice-germ-derived lipoxygenase.

2. Preparation of Flaxseed-Derived Allene Oxide Synthase

Acetone (250 mL) was added to flaxseeds (200 g) purchased from Ichimaru Pharcos Co., Ltd. The resultant mixture was homogenized (20 s×3), and the resultant precipitate was subjected to filtration by use of a perforated plate funnel, to thereby remove the solvent.

Subsequently, the precipitate was again suspended in acetone (250 mL), and the suspension was homogenized (10 s×3), to thereby yield a precipitate. The precipitate was washed with acetone and ethyl ether, and then dried, to thereby yield flaxseed powder (150 g).

The thus-yielded flaxseed powder (20 g) was suspended in a 50 mM phosphate buffer solution (pH 7.0) (400 mL) under cooling with ice. The resultant suspension was stirred by use of a stirrer at 4° C. for one hour to extraction.

The resultant extract was subjected to centrifugation at 11,000 rpm for 30 minutes. To the supernatant was added ammonium sulfate (105.3 g) (0-45% saturation), and the mixture was allowed to stand for one hour under cooling with ice. The mixture was further subjected to centrifugation at 11,000 rpm for 30 minutes, to thereby yield a precipitate. The precipitate was dissolved in a 50 mM phosphate buffer solution (pH 7.0) (150 mL), and the resultant solution was subjected to desalting through dialysis (3 L×3), to thereby yield a crude solution containing desired flaxseed-derived allene oxide synthase.

3. Preparation of α-Linolenic Acid Sodium Salt

α-Linolenic acid serving as a starting material has considerably low water solubility. Therefore, in order to cause α-linolenic acid to function effectively as an enzyme substrate, an α-linolenic acid sodium salt was prepared.

Specifically, sodium carbonate (530 mg) was dissolved in purified water (10 mL), and then heated to 55° C. α-Linolenic acid (product of Nacalai Tesque, Inc.) (278 mg) was added dropwise to the resultant solution, and the mixture was stirred for three hours.

After completion of reaction, the reaction mixture was neutralized with Dowex50W-X8 (H⁺ form) (product of Dow Chemical Co.), to thereby yield a precipitate. The precipitate was subjected to filtration to thereby remove a resin. Subsequently, the precipitate was dissolved in MeOH, and then the solvent was removed under vacuum.

The thus-obtained product was recrystallized with isopropanol, to thereby yield a desired α-linolenic acid sodium salt (250 mg, 83%).

4. Production of Specific Ketol Fatty Acid (I)

The α-linolenic acid sodium salt yielded above in 3 (15 mg: 50 μmol) was dissolved in a 0.1 M phosphate buffer solution (pH 7.0) (30 mL). To the resultant solution was added the rice-germ-derived lipoxygenase crude solution prepared above in 1 (3.18 mL) at 25° C. under oxygen flow, and the mixture was stirred for 30 minutes: The rice-germ-derived lipoxygenase crude solution (3.18 mL) was further added to the mixture, and the resultant mixture was stirred for 30 minutes.

After completion of stirring, the allene oxide synthase crude solution prepared above in 2 (34.5 mL) was added to the lipoxygenase reaction mixture under nitrogen flow, and the resultant mixture was stirred for 30 minutes. Thereafter, dilute hydrochloric acid was added to the reaction mixture under cooling by use of ice, to thereby adjust the pH of the mixture to 3.0.

Subsequently, the reaction mixture was subjected to extraction with a solvent mixture of $CHCl_3$ and MeOH (10:1). The thus-obtained organic layer was subjected to dehydration through addition of magnesium sulfate, and the solvent was removed under vacuum and then dried.

The thus-obtained crude product was subjected to HPLC, and a fraction corresponding to the peak of specific ketol fatty acid (I) (retention time: about 16 min.) was obtained. Chloroform was added to the thus-obtained fraction, the separated chloroform layer was washed with water, and the chloroform was removed by use of an evaporator, to thereby yield a purified product.

In order to confirm the structure of the purified product, the product was subjected to measurement of $^1$H- and $^{13}$C-NMR spectra by use of a heavy methanol solution.

As a result, in the $^1$H-NMR measurement, signals corresponding to an end methyl group [δ 0.98 (t)], two carbon-carbon double bonds [(δ 5.25, 5.40), (δ 5.55, 5.62)], a secondary hydroxyl group [δ 4.09 (dd)], and numerous methylene groups were observed, and the product was presumed to be specific ketol fatty acid (I).

Furthermore, the $^{13}$C-NMR chemical shifts of the product were identical to the $^{13}$C-NMR chemical shifts of specific ketol fatty acid (I) described in Japanese Patent Application Laid-Open (kokai) No. 10-324602 (in [0054] and [0055], from line 2 of column 13, page 8), the fatty acid being produced in "Production Example (extraction method)" described in the above publication (from last line of column 11, page 7) (see Table 1).

Thus, the synthesized product obtained by means of the above enzyme method was identified as 9-hydroxy-10-oxo-12 (Z),15(Z)-octadecadienoic acid.

TABLE 1

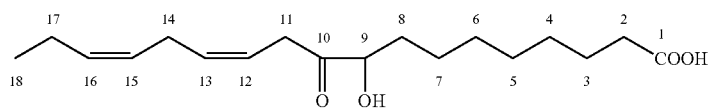

|  | Standard product | Product synthesized by means of enzyme method |
|---|---|---|
| C-1 | 178.5 | 178.4 |
| C-2 | 35.7 | 35.4 |
| C-3 | 26.8* | 26.9* |

TABLE 1-continued

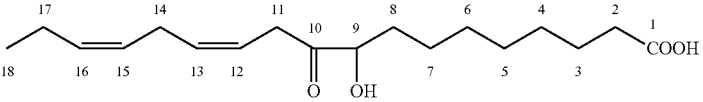

| | Standard product | Product synthesized by means of enzyme method |
|---|---|---|
| C-4 | 31.1** | 31.1** |
| C-5 | 31.0** | 31.0** |
| C-6 | 31.1** | 31.1** |
| C-7 | 26.9* | 26.9* |
| C-8 | 35.4 | 35.4 |
| C-9 | 78.6 | 78.6 |
| C-10 | 213.8 | 213.8 |
| C-11 | 38.4 | 38.4 |
| C-12 | 123.0 | 123.0 |
| C-13 | 133.5 | 133.4 |
| C-14 | 27.5 | 27.5 |
| C-15 | 128.4 | 128.4 |
| C-16 | 134.6 | 134.0 |
| C-17 | 22.3 | 22.3 |
| C-18 | 15.4 | 15.4 |

*, ** exchangeable

Test Example A

Evaluation of Plant Growth Promotion Effect of Specific Ketol Fatty Acid (I) (Growth Promotion Test)

1. Evaluation of Growth Promotion Effect on Morning Glory

Seeds of morning glory (variety: *murasaki*) (9 g) were subjected to concentrated sulfuric acid treatment for 20 minutes, and then allowed to stand under water flow overnight. Subsequently, the seeds were placed on wet sea sand such that the hila of the seeds were directed upward for 24 hours, to thereby produce roots. The seeds having roots were planted in sea sand at a position 1.5-2.0 cm below the surface of the sand, and then cultured under continuous light irradiation (for about five days).

The entire plant bodies of the morning glory having leaves produced through this culture were transferred into a culture solution [$KNO_2$ (250 mg), $NH_4NO_2$ (250 mg), $KH_2PO_4$ (250 mg), $MgSO_4.7H_2O$ (250 mg), $MnSO_4.4H_2O$ (1 mg), Fe-citrate n-hydrate (6 mg), $H_3BO_3$ (2 mg), $CuSO_4.5H_2O$ (0.1 mg), $ZeSO_4.7H_2O$ (0.2 mg), $Na_2MoO_4.2H_2O$ (0.2 mg), and $Ca(H_2PO_4)_2 2H_2O$ (250 mg) in distilled water (1,000 mL)].

Water or a 100 μm specific ketol fatty acid (I) aqueous solution was sprayed to the cultured morning glory, which was then placed in the dark overnight (for 14 hours). Thereafter, the morning glory was grown under continuous light irradiation at 25° C. for 16 days, and on the 16th day the height of the plant was measured (N=8). The average of the heights of the plants is shown in FIG. 1 [note: "I" shown in FIG. 1 refers to "specific ketol fatty acid (I)"; the same shall apply to the below-described Figs.]. As is clear from FIG. 1, the plant of the morning glory becomes larger through application of specific ketol fatty acid (I).

2. Evaluation of Growth Promotion Effect on Lettuce

Figure 2:
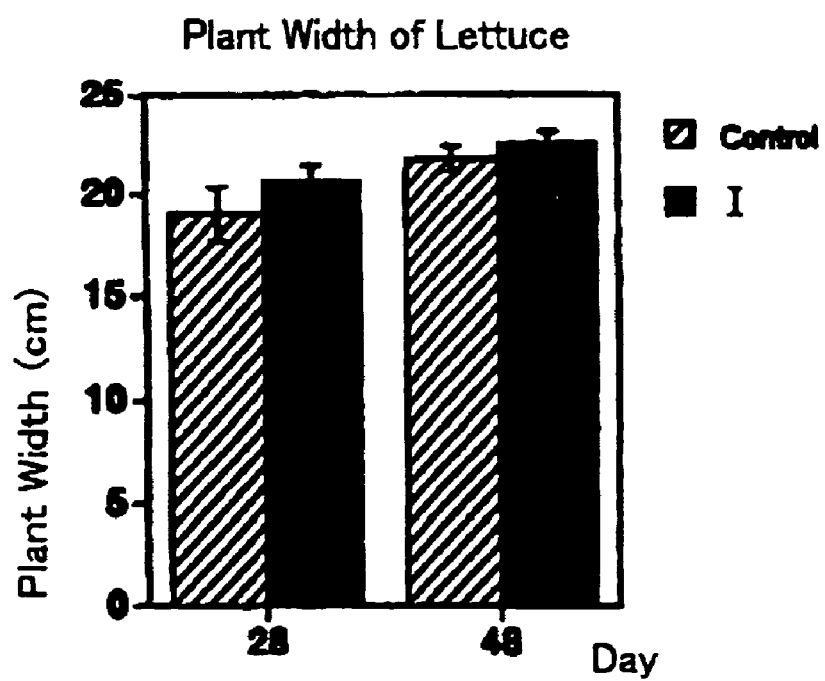
FIG. 2 shows the results of evaluation of growth promotion effect of specific ketol fatty acid (I) on lettuce.

One month after seeding of lettuce, spraying of a 50 μM specific ketol fatty acid (I) aqueous solution was carried out for five consecutive days, and growth of the lettuce (plant width) was observed. The results are shown in FIG. 2. As shown in FIG. 2, specific ketol fatty acid (I) exerts the effect of promoting growth of the lettuce. The growth promotion effect was maintained 48 days after the start of the test.

3. Evaluation of Growth Promotion Effect on Broad Bean

Figure 3:
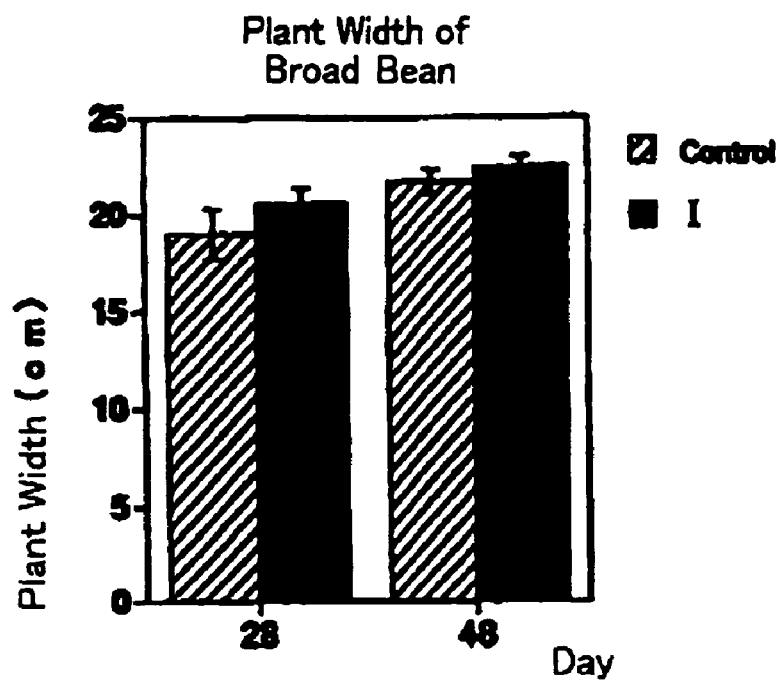
FIG. 3 shows the results of evaluation of growth promotion effect of specific ketol fatty acid (I) on broad bean.

One month after seeding of broad bean, spraying of a 50 μm specific ketol fatty acid (I) aqueous solution was carried out for five consecutive days, and growth of the broad bean (plant width) was observed. The results are shown in FIG. 3. As shown in FIG. 3, specific ketol fatty acid (I) exerts the effect of promoting growth of the broad bean. The growth promotion effect was maintained 48 days after the start of the test.

4. Evaluation of Growth Promotion Effect on *Eustoma Russellianum*

Figure 4:
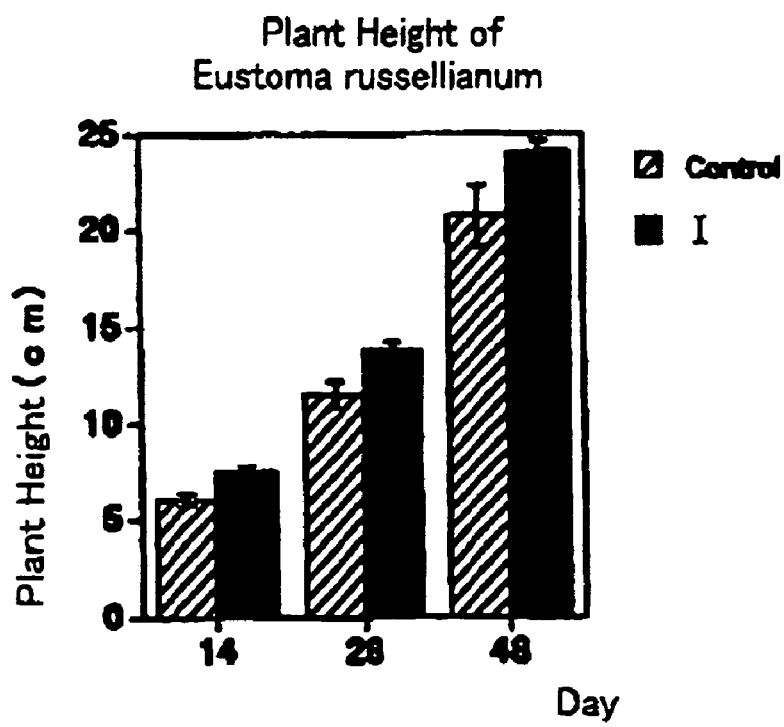
FIG. 4 shows the results of evaluation of growth promotion effect of specific ketol fatty acid (I) on *Eustoma russellianum*.

Three months after seeding of *Eustoma russellianum*, a 50 μm specific ketol fatty acid (I) aqueous solution was sprayed to rosette leaves for five consecutive days, and bolting was observed immediately after the spraying. Thereafter, growth of the plants of the *Eustoma russellianum* was observed for 48 days. Although plant width did not increase as had been expected, the plant height continued to increase 48 days after observation of growth. The results (plant height) are shown in FIG. 4.

5. Evaluation of Growth Promotion Effect on Cyclamen

Figure 5:
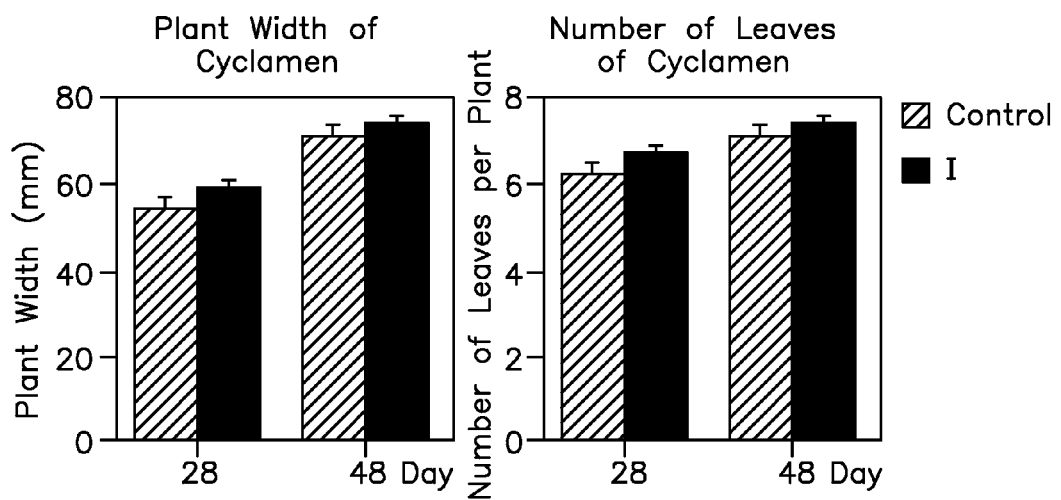
FIG. 5 shows the results of evaluation of growth promotion effect of specific ketol fatty acid (I) on cyclamen.

Four months after seeding of cyclamen, spraying of a 50 μm specific ketol fatty acid (I) aqueous solution was carried out for five consecutive days. Thereafter, the plant width and the number of leaves were observed for 48 days. The plant width and the number of leaves were both increased. The results are shown in FIG. 5.

6. Evaluation of Growth Promotion Effect on Digitalis

Figure 6:
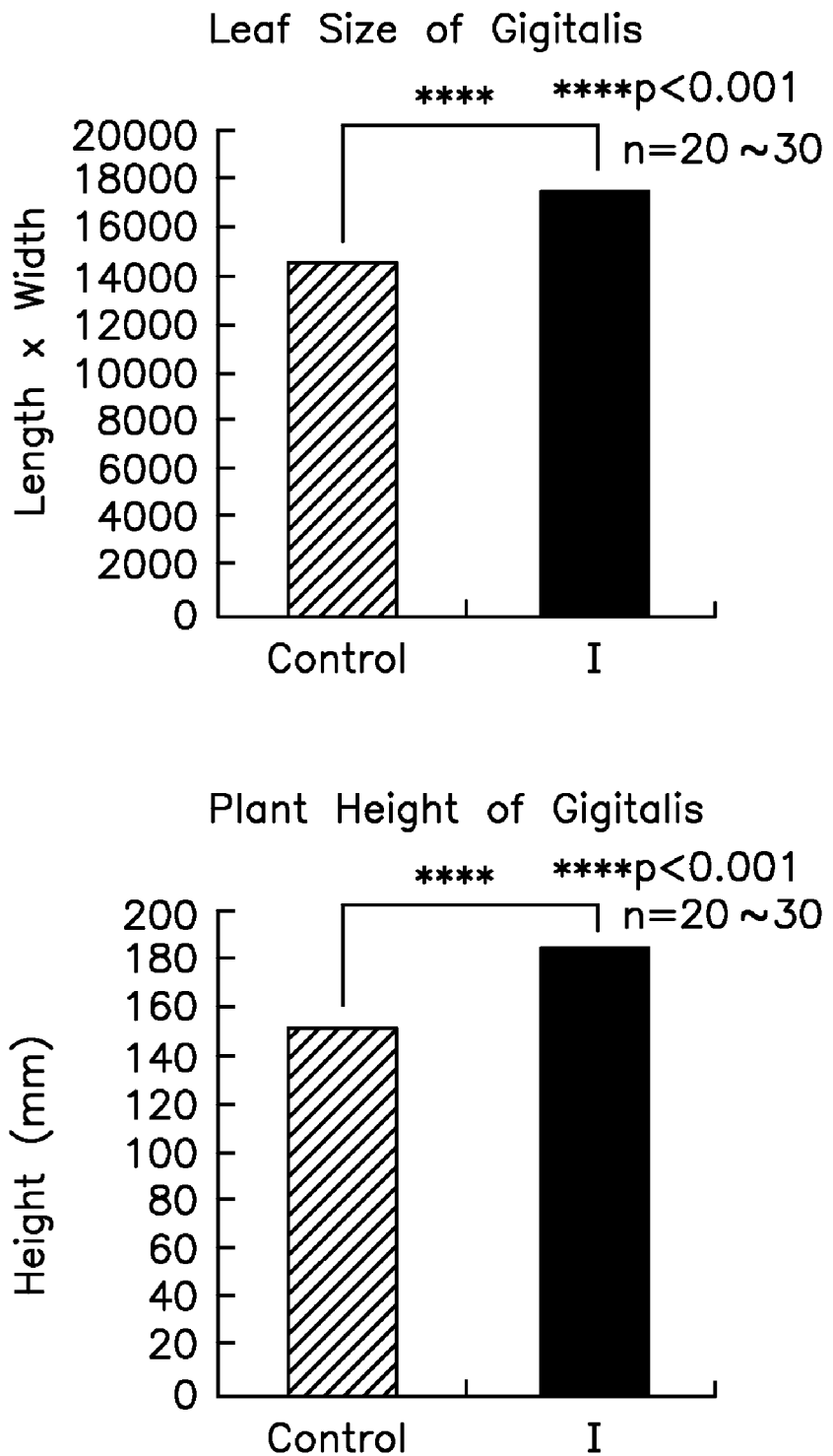
FIG. 6 shows the results of evaluation of growth promotion effect of specific ketol fatty acid (I) on digitalis.

Two weeks after seeding of digitalis, spraying of an 80 μm specific ketol fatty acid (I) aqueous solution was carried out for five consecutive days. Furthermore, three months after the start of the test; spraying of an 80 μm specific ketol fatty acid (I) aqueous solution was carried out for six weeks (once a week). Five-and-a-half months after the six-week spraying, the size of leaves and the plant height were measured. The results show that the size of leaves and the plant height were both increased (see FIG. 6).

7. Evaluation of Growth Promotion Effect on Chrysanthemum

Figure 7:
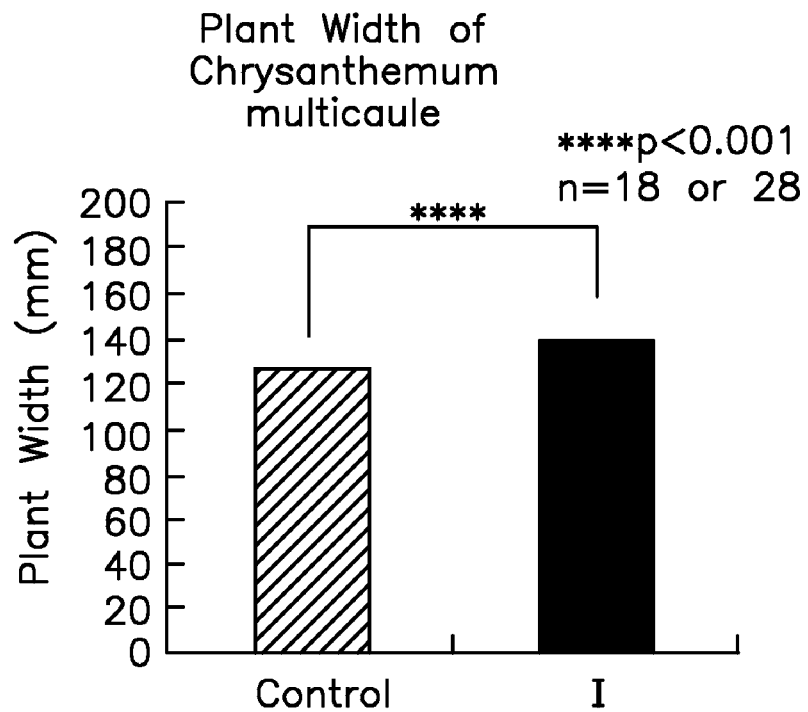
FIG. 7 shows the results of evaluation of growth promotion effect of specific ketol fatty acid (I) on chrysanthemum.

Two weeks after seeding of chrysanthemum, spraying of an 80 μm specific ketol fatty acid (I) aqueous solution was carried out for five consecutive days. Furthermore, three months after the start of the test, spraying of an 80 μM specific ketol fatty acid (I) aqueous solution was carried out for six weeks (once a week). Bolting was not observed at a nutrition growth stage of the chrysanthemum. Four months after the last spraying, the plant width was measured. The results show that the plant width of the chrysanthemum is increased significantly (see FIG. 7).

8. Evaluation of Growth Promotion Effect on Geranium

Figure 8:
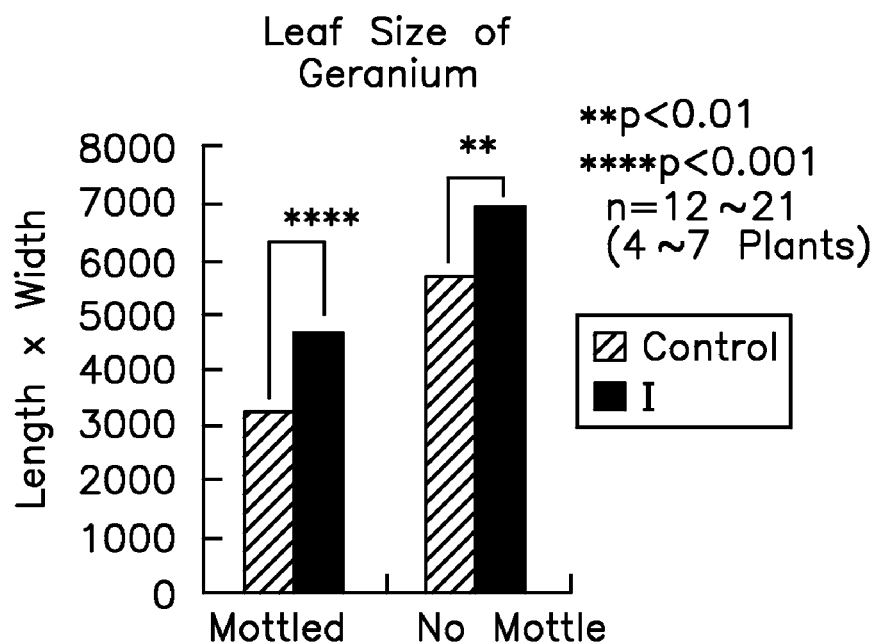
FIG. 8 shows the results of evaluation of growth promotion effect of specific ketol fatty acid (I) on geranium.

Two weeks after seeding of geranium, spraying of an 80 μM specific ketol fatty acid (I) aqueous solution was carried out for five consecutive days. Furthermore, three months after the start of the test, spraying of an 80 μM specific ketol fatty acid (I) aqueous solution was carried out for six weeks (once a week). Two types of geranium; i.e., geranium having mottled leaves and geranium having leaves of no mottles, were subjected to the test. Five-and-a-half months after the last spraying, the size of the leaves was measured. The results show that growth of the leaves of these two types is promoted (see FIG. 8).

9. Evaluation of Growth Promotion Effect on *Primula Melacoides*

Figure 9:
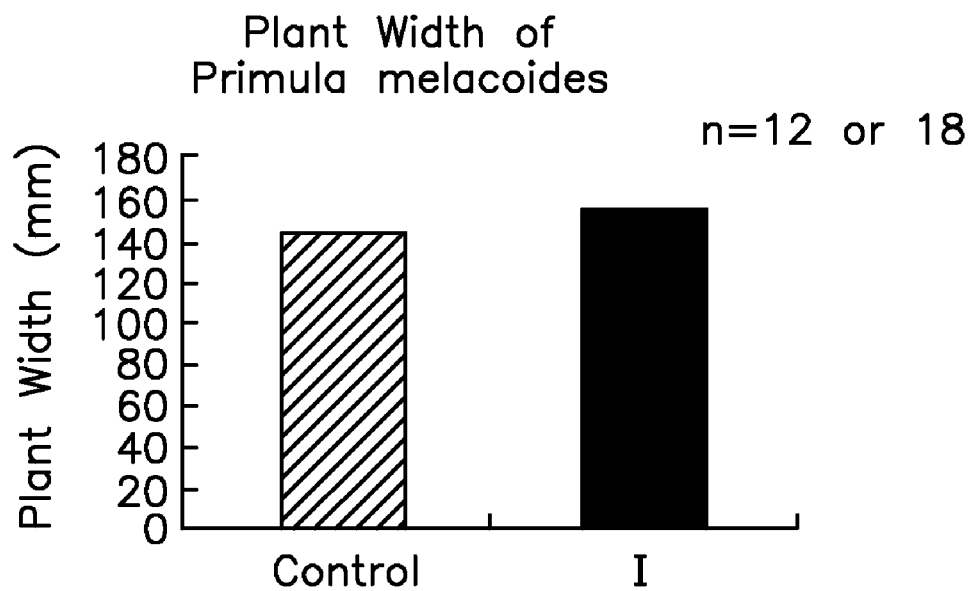
FIG. 9 shows the results of evaluation of growth promotion effect of specific ketol fatty acid (I) on *Primula melacoides*.

One-and-a-half months after seeding of *Primula melacoides*, spraying of an 80 μm specific ketol fatty acid (I) aqueous solution was carried out for five consecutive days. Furthermore, four months after the start of the test, spraying of an 80 μM specific ketol fatty acid (I) aqueous solution was carried out for six weeks (once a week). Bolting was not observed at a nutrition growth stage of the *Primula melacoides*. Six-and-a-half months after the last spraying, the plant width and the leave size were measured. The results show that the plant width and leave size of the chrysanthemum are increased (see FIG. 9).

10. Evaluation of Growth Promotion Effect on *Begonia Sempaflorens*

Figure 10:
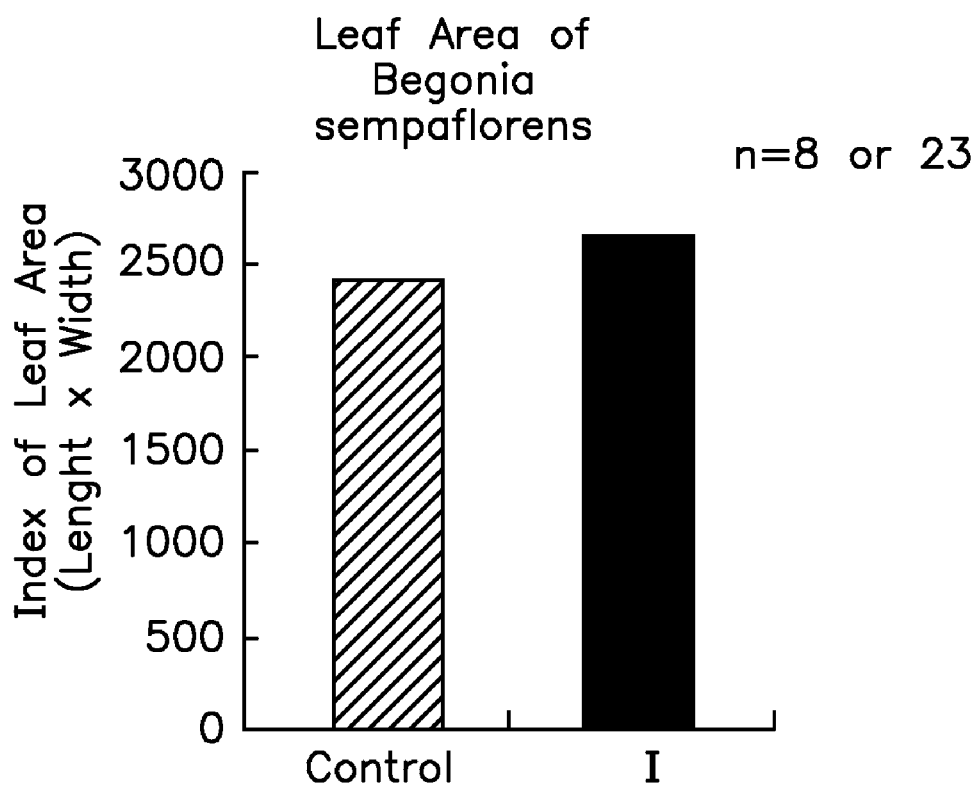
FIG. 10 shows the results of evaluation of growth promotion effect of specific ketol fatty acid (I) on *Begonia sempaflorens*.

Two weeks after seeding of *Begonia sempaflorens*, spraying of an 80 μm specific ketol fatty acid (I) aqueous solution was carried out for five consecutive days. Furthermore, three months after the start of the test, spraying of an 80 μm specific ketol fatty acid (I) aqueous solution was carried out for six weeks (once a week). Four months after the last spraying, the leave size was measured. The results show that growth of the leaves is promoted (see FIG. 10).

11. Evaluation of Growth Promotion Effect on *Dianthus Caryophyllus*

Figure 11:
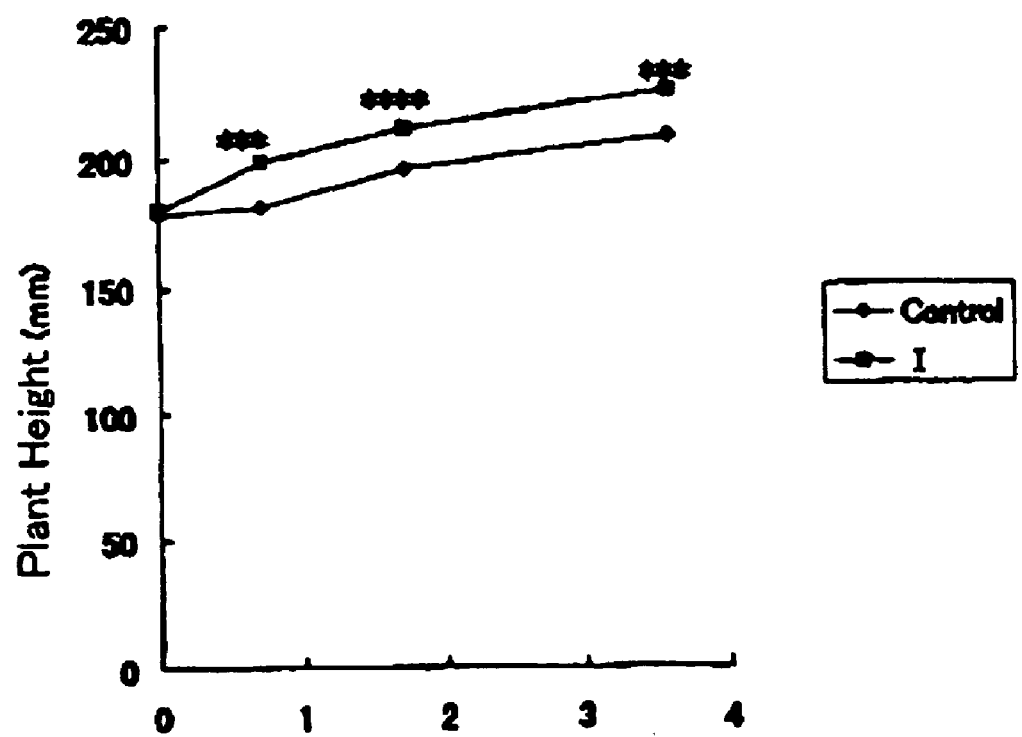
FIG. 11 shows the results of evaluation of growth promotion effect of specific ketol fatty acid (I) on *Dianthus caryophyllus*.

Seedlings of *Dianthus caryophyllus* (feeling scarlet) were planted in early October, and then grown by means of a customary method. In mid-April of the next year, spraying of a 100 μm specific ketol fatty acid (I) aqueous solution was carried out (5 mL per plant), and then the height of the plants was measured. The results show that growth of the *Dianthus caryophyllus* plant was promoted in the group to which the specific ketol fatty acid (I) had been applied, although spraying of the specific ketol fatty acid (I) had been carried out only once (see FIG. 11).

12. Evaluation of Growth Controlling Effect on *Oryza Sativa* L.

(1) Good-quality seeds of *Oryza sativa* L. (variety: *koshihikari*) (200 g) were immersed in water (800 mL) at 10° C. for 13 days. Thereafter, the seeds were equally divided into four groups, and the respective seed groups were immersed in specific ketol fatty acid (I) aqueous solutions (concentration: 0 μM, 1 μM, 10 μM, and 100 μM) (200 mL) at 30° C. for 1.5 days. The immersed seeds were planted in a four-divided seedbed tray, and grown under no light irradiation at 27° C. for three days. Subsequently, the grown seedlings were exposed to the typical outside environment.

Figure 12:
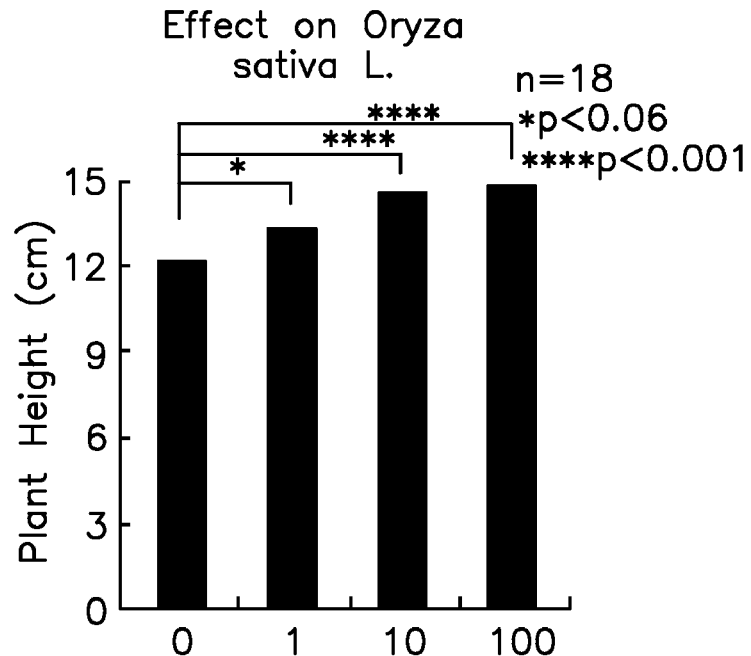
FIG. 12 shows the results of evaluation of growth promotion effect of specific ketol fatty acid (I) on *Oryza sativa* L.

Six days after the exposure, 18 seedlings were randomly selected from each group, and the heights of the seedlings were measured, and then averaged. The results are shown in FIG. 12. As shown in FIG. 12, the degree of growth promotion of the seedlings regarding the height is commensurate with the application amount of the specific ketol fatty acid (I).

Thus, the plant growth promotion effect of the present plant activator, which is confirmed in the aforementioned tests employing various plants, is also observed in *Oryza sativa* L.

Figure 13:
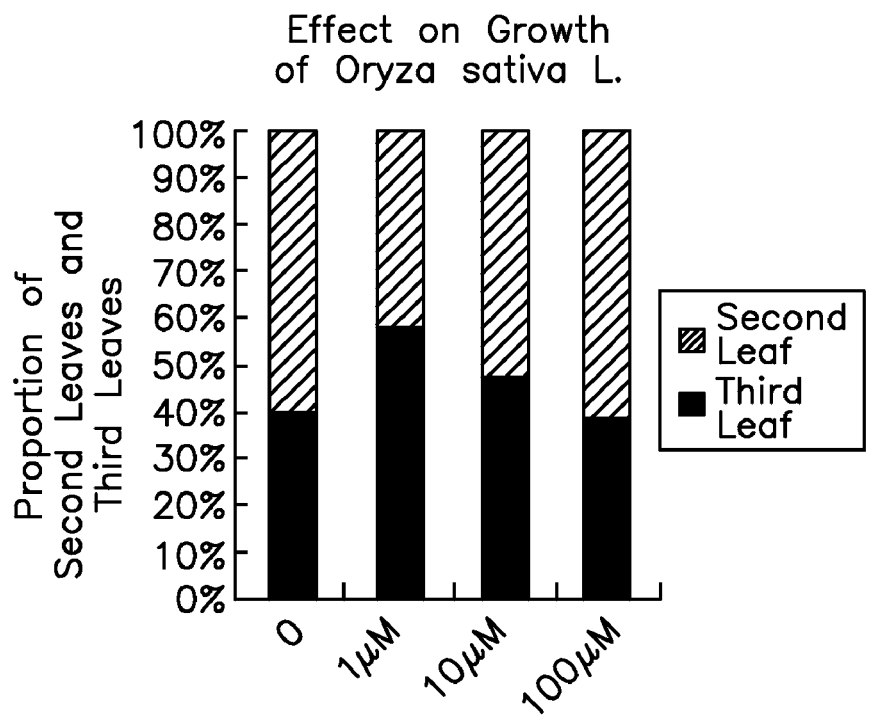
FIG. 13 shows the results of evaluation of growth controlling effect of specific ketol fatty acid (I) on *Oryza sativa* L. in consideration of practical culture.

Subsequently, in consideration of practical handling of seedlings of *Oryza sativa* L., the effect of application of specific ketol fatty acid (I) was evaluated. Specifically, whether or not specific ketol fatty acid (I) exerts the effect of controlling growth of the third leaves of seedlings of *Oryza sativa* L. was evaluated, since the time when the third leaves are grown in seedlings of *Oryza sativa* L. is considered to be a suitable time for transferring the seedlings from a seedbed to a paddy field. In order to perform this evaluation, three weeks after the aforementioned light irradiation treatment, seedlings of each group were randomly selected, and the average of the proportions of the second leaves and third leaves was obtained. The results are shown in FIG. 13. As shown in FIG. 13, specific ketol fatty acid (I) exerts the effect of controlling growth of the third leaves. However, unlike the case of promotion of growth of the seedlings, the optimum concentration of the specific ketol fatty acid (I) aqueous solution is 1 μM.

The results show that, when specific ketol fatty acid (I) is used as an active ingredient of the present plant activator in order to shorten the growth period of seedlings of *Oryza sativa* L. in a seedbed, the application amount of the specific ketol fatty acid (I) must be determined appropriately.

(2) Seedlings of *Oryza sativa* L. were grown in a seedbed in a manner similar to that described in (1), except that the seedlings were immersed in ion-exchange water at 10° C. for 15 days, without application of specific ketol fatty acid (I) described above in (1). Subsequently, the resultant seedlings which had been divided into five groups, each group containing three subgroups (only control group containing four subgroups) and each subgroup containing 16 seedlings, were exposed to the outside environment. Immediately after this exposure, spraying of specific ketol fatty acid (I) was carried out (0 ppm for a first group (control group), 25 ppm for second and third groups, 50 ppm for fourth and fifth groups). Thirty days after the spraying, the seedlings were planted in a paddy field, and additional spraying of specific ketol fatty acid (I) (25 ppm) was carried out for two groups; i.e., the third group (total amount of the acid (I): 25+25 ppm) and the fifth group (total amount of the acid (I): 50+25 ppm).

Subsequently, the seedlings of the *Oryza sativa* L. were grown in the paddy field by means of a customary method. Forty-one days after the above planting, in each group, the plant height and the number of stems per plant (at a section at which four seedlings were planted) were measured, and then averaged.

The plant height was 56 cm in the control group (first group), 57 cm in the second group (amount of the specific ketol fatty acid (I): 25 ppm), 58 cm in the fourth group (amount of the specific ketol fatty acid (I): 50 ppm), 57 cm in the third group (amount of the specific ketol fatty acid (I): 25+25 ppm), and 58 cm in the fifth group (amount of the specific ketol fatty acid (I): 50+25 ppm). Therefore, significant difference was not observed between these groups.

The number of stems per plant was 34 in the control group (first group), 38 in the second group (amount of the specific ketol fatty acid (I): 25 ppm), 38 in the fourth group (amount of the specific ketol fatty acid (I): 50 ppm), 39 in the third group (amount of the specific ketol fatty acid (I): 25+25 ppm), and 37 in the fifth group (amount of the specific ketol fatty acid (I): 50+25 ppm). Briefly, the number of stems per plant in each of the Second through fifth groups was about 10% greater than that of stems per plant in the control group. However, difference attributed to the application manner of the specific ketol fatty acid (I) was not observed.

The results show that specific ketol fatty acid (I) serving as an active ingredient of the present plant activator exerts the effect of controlling growth of *Oryza sativa* L.; i.e., the effect of increasing the number of stems. Therefore, the specific ketol fatty acid (I) exerts the effect of increasing the yield of rice on the basis of unit area of the paddy field in which the seedlings are planted; i.e., an considerably important effect in production of rice.

The results of the aforementioned growth promotion tests show that specific ketol fatty acid (I) exerts excellent effect of promoting growth of various forms of many plants. Particularly, the specific ketol fatty acid (I) exerts the effect of promoting growth of a plant in an early stage of its growth, and the growth promotion effect is continuous.

Thus, it is apparent that specific ketol fatty acid (1) serving as an active ingredient of the present plant activator exerts the effect of promoting growth of various plants, and the present plant activator is useful.

As described above, it is clear that the present plant activator can be used as a plant growth promoting agent or a plant growth controlling agent.

Test Example B

Evaluation of Plant Dormancy Preventive Effect of Specific Ketol Fatty Acid (I) (Plant Dormancy Preventive Test When strawberry seedlings are exposed directly to low temperature conditions in winter, the seedlings enter dormancy, and growth of the seedlings is stopped. Whether or not the present plant activator exerts the effect of preventing dormancy was evaluated.

Specific ketol fatty acid (I) aqueous solutions [concentration: 10 µM, 100 µM, and 0 µM (control)] were applied through spraying to strawberry seedlings on August 27 (at day 0), September 3, and September 8. Thereafter, the seedlings were cultured outdoors without artificial treatment such as low temperature treatment, and formation of flower buds was observed with passage of time. In the control group, no flower bud formation was observed. In contrast, in the groups in which the specific ketol fatty acid (I) was applied through spraying, flower bud formation proceeded, and the number of flowers increased (this flower bud formation promotion effect agrees with the description of Japanese Patent Application Laid-Open (kokai) No. 11-29410).

Figure 14:
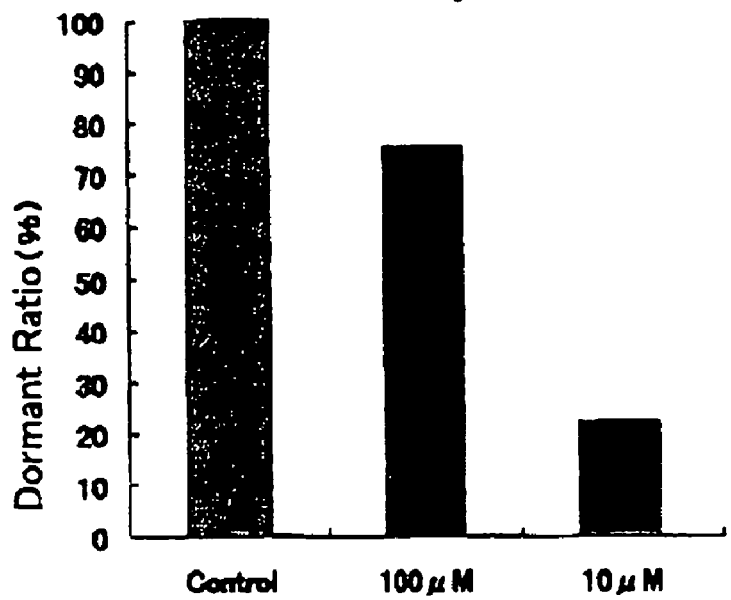
FIG. 14 shows the results of evaluation of dormancy preventive effect of specific ketol fatty acid (I) on strawberry.

At the one hundred and eighth day, percent dormancy (percentage of dormant plants—which are plants in which growth of small leaf buds with markings is not observed 15 days after a marking was applied to the leaf buds—with respect to the entirety of the test plants) was measured. As a result, in the control group, dormancy of the entire plants was observed. In contrast, in the groups in which the specific ketol fatty acid (I) aqueous solution was applied through spraying, dormancy of strawberry was prevented. The results show that the dormancy preventive effect is more significant in the group in which the specific ketol fatty acid (I) of low concentration (10 µm) was applied than in the group in which the fatty acid (I) of high concentration (100 µM) was applied (see FIG. 14).

The results show that when the present plant activator of low concentration is applied to a plant, the activator exerts the effect of preventing dormancy of the plant; the activator can be used as a plant dormancy preventive agent or a plant growth controlling agent; and the activator is useful.

Test Example C

Evaluation of Plant Stress (Dry Stress) Suppressive Effect of Specific Ketol Fatty Acid (I)

Seeds of lettuce (50 seeds per test group) were immersed in specific ketol fatty acid (I) aqueous solutions [concentration: 2 µM, 10 µM, 20 µM, and 0 µM (control)] for 72 hours, and dried in air for 48 hours. The resultant seeds were disposed on water-containing filter paper, and allowed to germinate. In each test group, germination rate—percentage (%) of germinated seeds with respect to the entirety of seeds—was obtained.

The results are shown in Table 2.

TABLE 2

| Specific ketol fatty acid (I) concentration (µM) | Germination rate (%: n = 50) | Number of germinated seeds |
| --- | --- | --- |
| 0 | 10 | 5 |
| 2 | 86 | 43 |
| 10 | 98 | 49 |
| 20 | 90 | 45 |

As is apparent from the results, in the control group, most seeds failed to endure the dry stress in the drying step, resulting in failure of germination. In contrast, most of the seeds which had been immersed in the specific ketol fatty acid (I) aqueous solution successfully germinated.

From the above results, it is clear that the present plant activator exerts the effect of enhancing tolerance of plants against dry stress; the activator can be used as a plant stress suppressing agent or a plant growth controlling agent; and the activator is useful.

Test Example D

Figure 15:
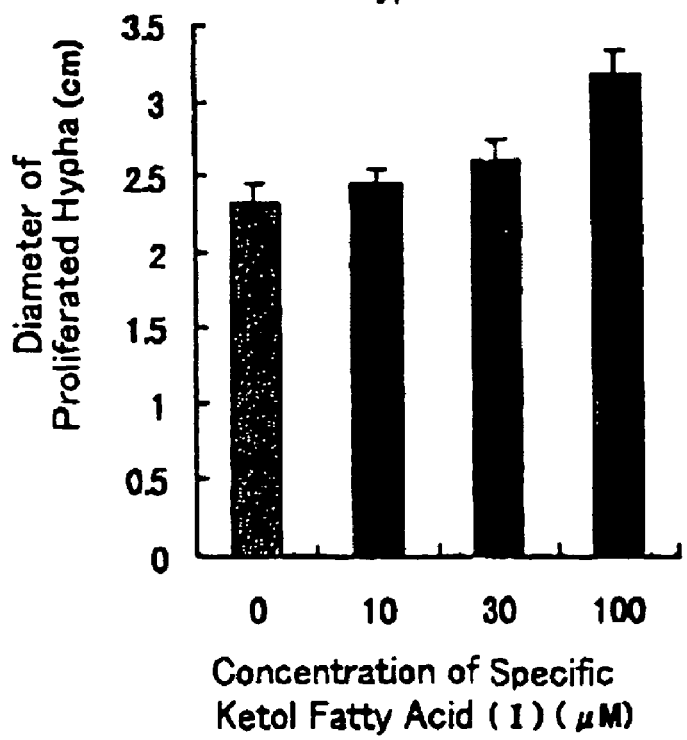
FIG. 15 shows the results of evaluation of proliferation enhancing effect of specific ketol fatty acid (I) on hyphae of *Pleurotus citrinopileatus* Sing.

Growth Controlling Effect of Specific Ketol Fatty Acid (I) on Fungi (1) Evaluation of Effect of Proliferating Hyphae of *P. Citrinopileatus* Sing. (Edible Mushroom) Belonging to *Pleurotus* Of Basidiomycota A potato-dextrose-agar culture medium was sterilized by use of an autoclave. After the medium was cooled to a temperature at which the agar was not solidified, a 1 mM specific ketol fatty acid (I) aqueous solution which had been sterilized by use of a membrane filter was added to the medium, to thereby prepare four culture media; i.e., a culture medium containing 0 µM of the fatty acid (I), a culture medium containing 10 µM of the fatty acid (I), a culture medium containing 30 µM of the fatty acid (I), and a culture medium containing 100 µm of the fatty acid (I). Each of the culture media was solidified in a 10-cm plate, and then hyphae of *P. citrinopileatus* (one platinum loop) was inoculated on the medium. Subsequently, the hyphae were cultured at 37° C., and proliferation of the hyphae was observed (10 plates for each group). Proliferation of the hyphae was evaluated on the basis of the average of the diameters of the proliferated hyphae on the plate. The results are shown in FIG. 15. As is clear from FIG.

15, the degree of proliferation of the hyphae of *P. citrinopileatus* is dependent on the concentration of the specific ketol fatty acid (i).

Figure 16:
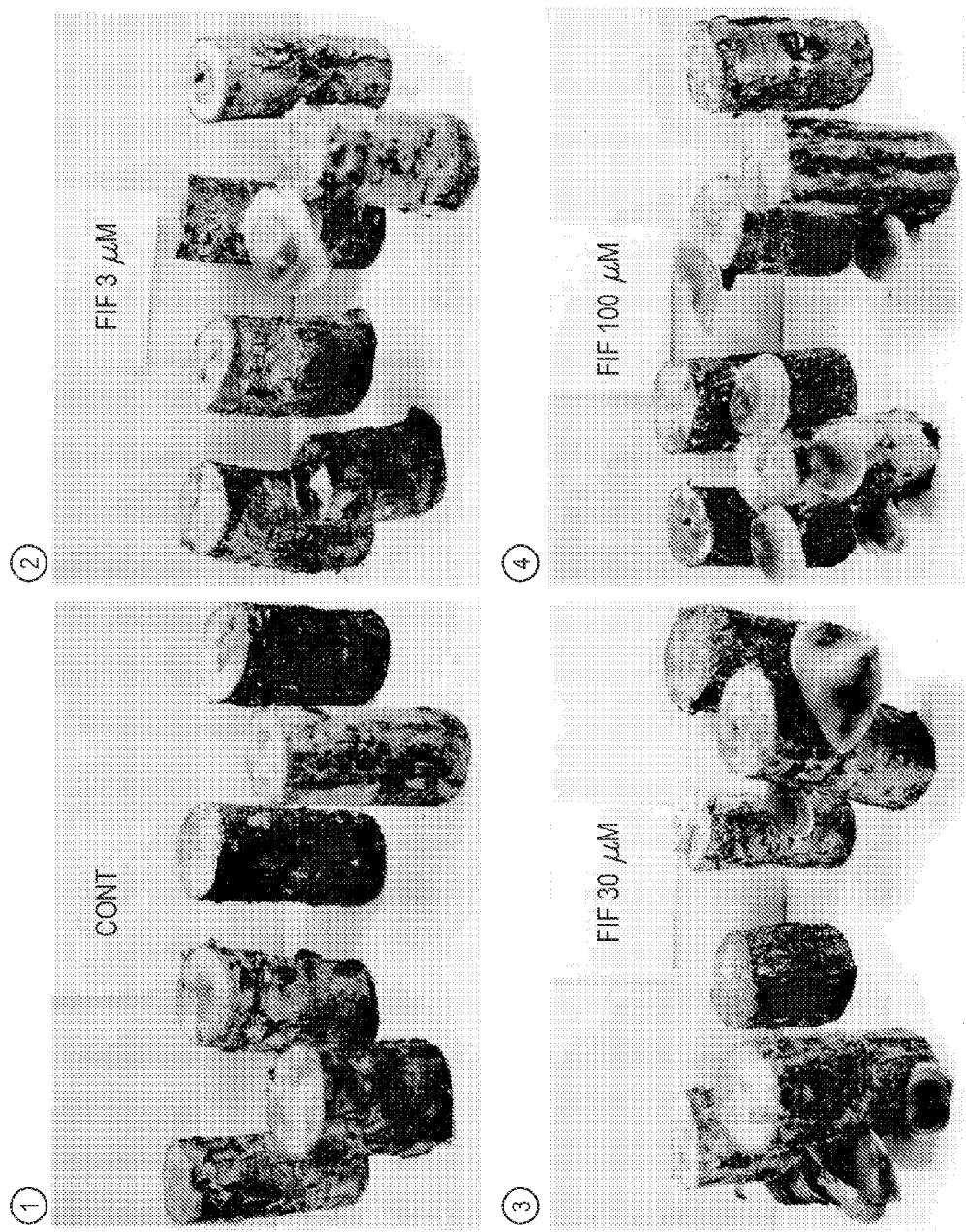
FIG. 16 is a photograph showing the results of evaluation of growth promotion effect of specific ketol fatty acid (I) on carpophore of *Lentinu edodes* (Berk.) Singer.

(2) Evaluation of Growth Promotion Effect on Carpophore Of *Lentinus edodes* (Berk.) Singer Wood (*Quercus serrata*) containing hyphae of *Lentinus edodes* was cut into pieces having a length of about 15 cm, and the pieces were immersed in 10° C. water for 24 hours, after which the pieces were allowed to stand in a container of high humidity. Subsequently, specific ketol fatty acid (I) aqueous solutions (concentration: 0 μm, 3 μM, 30 μm, and 100 μM) were applied through spraying to the resultant pieces (six pieces for each group). Each solution was applied to each group (5 mL for each piece). Subsequently, the carpophores of *Lentinus edodes* were cultured in the same container at 18° C. under weak light irradiation. This culture was continued for five days, and then growth of the carpophores of *Lentinus edodes* was observed. FIG. 16 is a photograph showing the carpophores of *Lentinus edodes* cultured in the groups (note: ① application of the specific ketol fatty acid (I) (0 μM), ② (3 μM), ③. (30 μM), and ④ (100 μM)). The average of the carpophores per piece was 0 in the 0 μM application group, 0.17 in the 3 μM application group, 1.0 in the 30 μM application group, and 1.0 in the 100 μM application group.

The results show that specific ketol fatty acid (I) exerts the effect of promoting growth of carpophores of *Lentinus edodes* during culture.

The results of the aforementioned tests (1) and (2) show that when specific ketol fatty acid (I) is applied to ascomycete or basidiomycete, proliferation of hyphae thereof can be promoted, and harvest efficiency of carpophores can be enhanced. Furthermore, the present plant activator may contribute to establishment of an artificial culture method of mushrooms which at present are difficult to culture artificially (e.g., *Tricholoma matsutake*).

INDUSTRIAL APPLICABILITY

As described above, the present invention provides a plant activator exerting excellent effect of controlling growth of various plants.

The invention claimed is:

1. A method of preventing dormancy of a plant, comprising applying to the plant an agent comprising a $C_{18}$-$C_{24}$ ketol fatty acid after germination,
said $C_{18}$-$C_{24}$ ketol fatty acid containing a carbon atom constituting a carbonyl group and a carbon atom connected to a hydroxyl group, one of the above carbon atoms being located at the α or γ position with respect to the other carbon atom,
wherein the plant's dormancy period is prevented.

2. The method according to claim 1, wherein said one of the carbon atoms is located at the α position with respect to said other carbon atom.

3. The method according to claim 2, wherein the $C_8$-$C_{24}$ ketol fatty acid contains one to six carbon-carbon double bonds, such that the number of the double bonds does not exceed the number of carbon-carbon bonds in the ketol fatty acid.

4. The method according to claim 2, wherein the ketol fatty acid contains 18 carbon atoms, and two carbon-carbon double bonds.

5. The method according to claim 2, wherein the $C_{18}$-$C_{24}$ ketol fatty acid is 9-hydroxy-10-oxo-12(Z),15(Z)-octadecadienoic acid.

6. A method of enhancing tolerance of a plant against stress, comprising applying to the plant an agent comprising a $C_{18}$-$C_{24}$ ketol fatty acid during or after germination of its seed,
said $C_{18}$-$C_{24}$ ketol fatty acid containing a carbon atom constituting a carbonyl group and a carbon atom connected to a hydroxyl group, one of the above carbon atoms being located at the α or γ position with respect to the other carbon atom,
wherein the effects of stress imposed on the plant are suppressed.

7. The method according to claim 6, wherein said one of the carbon atoms is located at the α position with respect to said other carbon atom.

8. The method according to claim 7, wherein the stress is dry stress.

9. The method according to claim 7, wherein the $C_{18}$-$C_{24}$ ketol fatty acid contains one to six carbon-carbon double bonds, such that the number of the double bonds does not exceed the number of carbon-carbon bonds in the ketol fatty acid.

10. The method according to claim 7, wherein the ketol fatty acid contains 18 carbon atoms, and two carbon-carbon double bonds.

11. The method according to claim 7, wherein the $C_{18}$-$C_{24}$ ketol fatty acid is 9-hydroxy-10-oxo-12(Z),15(Z)-octadecadienoic acid.

12. A method of activating a dormant plant, comprising applying to the dormant plant an agent comprising a $C_{18}$-$C_{24}$ ketol fatty acid after germination,
said $C_{18}$-$C_{24}$ ketol fatty acid containing a carbon atom constituting a carbonyl group and a carbon atom connected to a hydroxyl group, one of the above carbon atoms being located at the α position with respect to the other carbon atom,
wherein the plant's dormancy is terminated.

* * * * *